United States Patent
Garg et al.

(10) Patent No.: US 7,153,997 B2
(45) Date of Patent: Dec. 26, 2006

(54) BENZAMIDE DERIVATIVES AS THYROID RECEPTOR LIGANDS

(75) Inventors: Neeraj Garg, Tumba (SE); Mahmoud Rahimi Ghadim, Stockholm (SE); Thomas Anders Wilson Ericsson, Södertäwg (SE); Lars Johan Malm, Trangsund (SE); Denis Evan Ryono, Princeton, NJ (US)

(73) Assignees: Karo Bio AB, Huddinge (SE); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/520,902

(22) PCT Filed: Jul. 8, 2003

(86) PCT No.: PCT/EP03/07333

§ 371 (c)(1),
(2), (4) Date: Dec. 7, 2005

(87) PCT Pub. No.: WO2004/007430

PCT Pub. Date: Jan. 22, 2004

(65) Prior Publication Data

US 2006/0135614 A1    Jun. 22, 2006

(30) Foreign Application Priority Data

Jul. 10, 2002  (GB) ................... 0215978.8

(51) Int. Cl.
*C07C 229/08*  (2006.01)
*A61K 31/195*  (2006.01)

(52) U.S. Cl. ............... 562/444; 562/442; 562/443; 562/445; 562/447; 514/563

(58) Field of Classification Search ............ 562/442, 562/443, 444, 445, 447; 514/563
See application file for complete search history.

(56) References Cited

U.S. PATENT DOCUMENTS 6,395,784 B1 *  5/2002  Ryono .................. 514/563

FOREIGN PATENT DOCUMENTS

| WO | WO 00/39077    | 7/2000  |
| WO | WO 01/94293 A2 | 12/2001 |
| WO | WO 02/094319 A1| 11/2002 |

OTHER PUBLICATIONS

J. March: Chemical Abstracts, vol. 57, No. 7, p. 2493, Oct. 1, 1962.

* cited by examiner

*Primary Examiner*—Shailendra Kumar
(74) *Attorney, Agent, or Firm*—Todd E. Garabedian; Wiggin and Dana LLP

(57) ABSTRACT

This invention relates to novel compounds, which are thyroid receptor ligands, and to methods of preparing such compounds. In addition, a method is provided for preventing, inhibiting or treating diseases or disorders associated with metabolism dysfunction or which are dependent upon the expression of a T3 regulated gene, wherein a compound as described herein is administered in a therapeutically effective amount.

9 Claims, No Drawings

BENZAMIDE DERIVATIVES AS THYROID RECEPTOR LIGANDS

CROSS REFERENCE TO RELATED APPLICATIONS

This application is a U.S. National Stage application of International Application No. PCT/EP2003/007333 filed on Jul. 8, 2003.

FIELD OF THE INVENTION

This invention relates to novel compounds which are thyroid receptor ligands, and to methods of preparing such compounds and to methods for using such compounds such as in the regulation of metabolism.

BACKGROUND OF THE INVENTION

While the extensive role of thyroid hormones in regulating metabolism in humans is well recognized, the discovery and development of new specific drugs for improving the treatment of hyperthyroidism and hypothyroidism has been slow. This has also limited the development of thyroid agonists and antagonists for treatment of other important clinical indications, such as hypercholesterolemia, obesity and cardiac arrhythmias.

Thyroid hormones affect the metabolism of virtually every cell of the body. At normal levels, these hormones maintain body weight, metabolic rate, body temperature and mood, and influence blood levels of serum low density lipoprotein (LDL). Thus, in hypothyroidism there is weight gain, high levels of LDL cholesterol, and depression. In hyperthyroidism, these hormones lead to weight loss, hypermetabolism, lowering of serum LDL levels, cardiac arrhythmias, heart failure, muscle weakness, bone loss in postmenopausal women, and anxiety.

Thyroid hormones are currently used primarily as replacement therapy for patients with hypothyroidism. Therapy with L-thyroxine returns metabolic functions to normal and can easily be monitored with routine serum measurements of levels of thyroid-stimulating hormone (TSH), thyroxine (3,5,3',5'-tetraiodo-L-thyronine, or $T_4$) and triiodothyronine (3,5,3'-triiodo-L-thyronine, or $T_3$). However, replacement therapy, particularly in older individuals, may be restricted by certain detrimental effects from thyroid hormones.

In addition, some effects of thyroid hormones may be therapeutically useful in non-thyroid disorders if adverse effects can be minimized or eliminated. These potentially useful influences include weight reduction, lowering of serum LDL levels, amelioration of depression and stimulation of bone formation. Prior attempts to utilize thyroid hormones pharmacologically to treat these disorders have been limited by manifestations of hyperthyroidism, and in particular by cardiovascular toxicity.

Furthermore, useful thyroid agonist drugs should minimize the potential for undesired consequences due to locally induced hypothyroidism, i.e. sub-normal levels of thyroid hormone activity in certain tissues or organs. This can arise because increased circulating thyroid hormone agonist concentrations may cause the pituitary to suppress the secretion of thyroid stimulating hormone (TSH), thereby reducing thyroid hormone synthesis by the thyroid gland (negative feedback control). Since endogenous thyroid hormone levels are reduced, localized hypothyroidism can result wherever the administered thyroid agonist drug fails to compensate for the reduction in endogenous hormone levels in specific tissues. For example, if the thyroid agonist drug does not penetrate the blood-brain barrier, the effects of TSH suppression can lead to CNS hypothyroidism and associated risks such as depression.

Development of specific and selective thyroid hormone receptor ligands, particularly agonists of the thyroid hormone receptor could lead to specific therapies for these common disorders, while avoiding the cardiovascular and other toxicity of native thyroid hormones. Tissue-selective thyroid hormone agonists may be obtained by selective tissue uptake or extrusion, topical or local delivery, targeting to cells through other ligands attached to the agonist and targeting receptor subtypes. Tissue selectivity can also be achieved by selective regulation of thyroid hormone responsive genes in a tissue specific manner.

Accordingly, the discovery of compounds that are thyroid hormone receptor ligands, particularly selective agonists of the thyroid hormone receptor, may demonstrate a utility for the treatment or prevention of diseases or disorders associated with thyroid hormone activity, for example: (1) replacement therapy in elderly subjects with hypothyroidism who are at risk for cardiovascular complications; (2) replacement therapy in elderly subjects with subclinical hypothyroidism who are at risk for cardiovascular complications; (3) obesity; (4) hypercholesterolemia due to elevations of plasma LDL levels; (5) depression; and (6) osteoporosis in combination with a bone resorption inhibitor.

SUMMARY OF THE INVENTION

In accordance with the illustrative embodiments and demonstrating features of the present invention, compounds are provided which are thyroid receptor ligands, and have the general formula I:

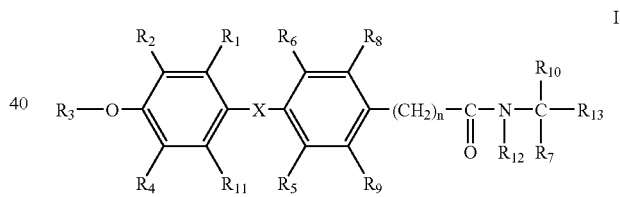

or a pharmaceutically acceptable salt thereof, wherein:

$R_1$ is selected from a group consisting of hydrogen, halogen, and $C_1$ to $C_6$ alkyl;

$R_2$ is selected from the group consisting of halogen, $C_1$ to $C_6$ alkyl, $C_2$ to $C_6$ alkenyl, $C_2$ to $C_6$ alkynyl, $C_4$ to $C_7$ cycloalkenyl, $C_3$ to $C_7$ cycloalkoxy, $SO_2(NR_{14}R_{15})$, $N(R_{16})SO_2R_{17}$, $SR_{17}$, $SOR_{17}$, $SO_2R_{17}$, $COR_{16}$, and $CR_{18}(OR_{16})R_{19}$; or $R_2$ is hydrogen when $R_4$ is alkyl and $R_1$ is halogen;

$R_3$ is selected from the group consisting of hydrogen, alkyl, benzyl, aroyl, and alkanoyl;

$R_4$ is halogen, cyano or alkyl;

$R_5$ and $R_6$ are independently selected from hydrogen, halogen; cyano, $C_{1-4}$ alkyl, $C_3$ to $C_6$ cycloalkyl; where at least one of $R_5$ and $R_6$ is not hydrogen;

$R_7$ and $R_{10}$ are independently selected from hydrogen, halogen, aryl and alkyl, and $R_7$ and $R_{10}$ may be joined so as to comprise a chain of 2 to 6 methylene groups to form a ring of 3 to 7-membered in size;

$R_8$ and $R_9$ are each independently selected from the group consisting of hydrogen, halogen, alkoxy, hydroxy (OH), cyano, and alkyl;

provided that not more than one of $R_2$, $R_4$, $R_8$ and $R_9$ are hydrogen;

$R_{11}$ is hydrogen, halogen or alkyl;

$R_{12}$ is hydrogen or alkyl;

$R_{13}$ is carboxylic acid (COOH) or esters thereof, phosphonic and phosphinic acid or esters thereof, sulfonic acid, tetrazole, hydroxamic acid, thiazolidinedione, acylsulfonamide, or other carboxylic acid surrogates known in the art;

$R_{14}$ and $R_{15}$ for each occurrence are each independently selected from the group consisting of hydrogen, alkyl, cycloalkyl, aryl, heteroaryl, arylalkyl and heteroarylalkyl, and $R_{14}$ and $R_{15}$ may be joined so as to comprise a chain of 3 to 6 methylene groups to form a ring of 4 to 7-membered in size;

$R_{16}$ is selected from a group consisting of hydrogen, alkyl, cycloalkyl, aryl, heteroaryl, arylalkyl and heteroarylalkyl;

$R_{17}$ is selected from a group consisting of alkyl, cycloalkyl, aryl, heteroaryl, arylalkyl and heteroarylalkyl;

$R_{18}$ and $R_{19}$ for each occurrence are each independently selected from the group consisting of hydrogen, alkyl, cycloalkyl, aryl, heteroaryl, arylalkyl and heteroarylalkyl;

n is an integer of 0, 1 or 2;

X is selected from: —O—, —$CH_2$—, —$CF_2$—, —Se—, —NH—, —S—, —SO—, —$SO_2$— and —CO—;

The definition of formula I above includes all prodrugs, stereoisomers and pharmaceutically acceptable salts of formula I.

The compounds of formula I are thyroid hormone receptor ligands and include compounds which are, for example, selective agonists, partial agonists, antagonists or partial antagonists of the thyroid receptor. Preferably, the compounds of formula I possess activity as agonists of the thyroid receptor, and may be used in the treatment of diseases or disorders associated with thyroid receptor activity. In particular, the compounds of formula I may be used in the treatment of diseases or disorders associated with metabolism dysfunction or which are dependent upon the expression of a $T_3$ regulated gene, such as obesity, hypercholesterolemia, atherosclerosis, cardiac arrhythmias, depression, osteoporosis, hypothyroidism, goiter, thyroid cancer, glaucoma, skin disorders or diseases and congestive heart failure.

The present invention provides for compounds of formula I, pharmaceutical compositions employing such compounds and for methods of using such compounds. In particular, the present invention provides for a pharmaceutical composition comprising a therapeutically effective amount of a compound of formula I, alone or in combination with a pharmaceutically acceptable carrier.

Further, in accordance with the present invention, a method is provided for preventing, inhibiting or treating the progression or onset of diseases or disorders associated with the thyroid receptor, such as the diseases or disorders defined above and hereinafter, wherein a therapeutically effective amount of a compound of formula I is administered to a mammalian, e.g., human patient in need of treatment.

The compounds of the invention can be used alone, in combination with other compounds of the present invention, or in combination with one or more other agent(s) active in the therapeutic areas described herein.

In addition, a method is provided for preventing, inhibiting or treating the diseases as defined above and hereinafter, wherein a therapeutically effective amount of a combination of a compound of formula I and another compound of the invention and/or another type of therapeutic agent, is administered to a mammalian patient in need of treatment.

Compounds of the invention include, but are not limited to, the following:

N-[3,5-Dichloro-4-(4-hydroxy-3-isopropyl-5-methylphenoxy)benzoyl]glycine (E1);

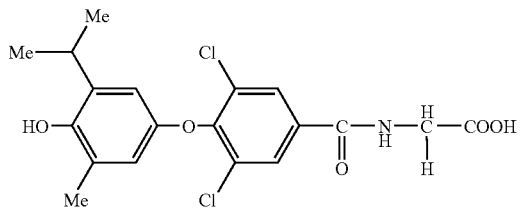

N-[3,5-Dichloro-4-(3-bromo-4-hydroxy-5-isopropylphenoxy)benzoyl]glycine (E2);

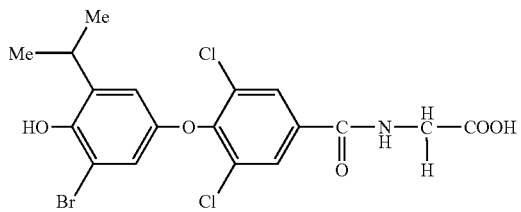

N-[3,5-Dichloro-4-(2-bromo-4-hydroxy-5-isopropylphenoxy)benzoyl]glycine (E3);

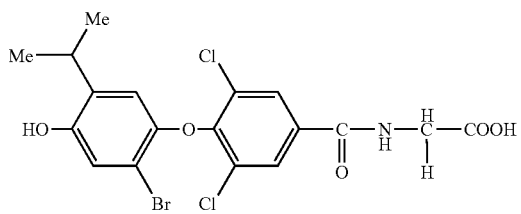

N-[3,5-Dichloro-4-(3-chloro-4-hydroxy-5-isopropylphenoxy)benzoyl]glycine (E4);

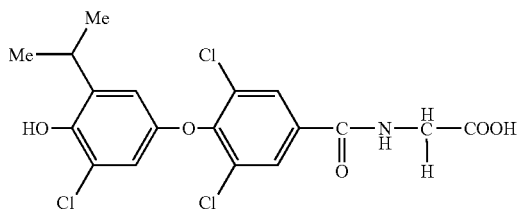

N-[3,5-Dichloro-4-(3-cyano-4-hydroxy-5-isopropylphenoxy)benzoyl]glycine (E5);

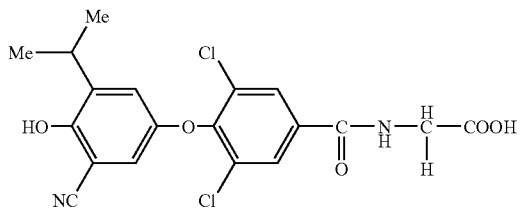

N-[3,5-Dichloro-4-(3-fluoro-4-hydroxy-5-isopropylphenoxy)benzoyl]glycine (E6);

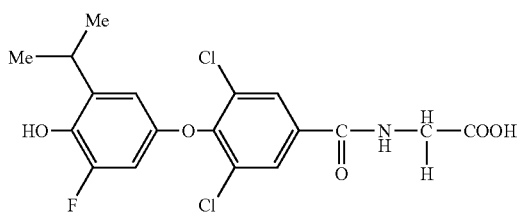

N-[3,5-Dichloro-2-methyl-4-(3-methyl-4-hydroxy-5-isopropylphenoxy)benzoyl]glycine (E7);

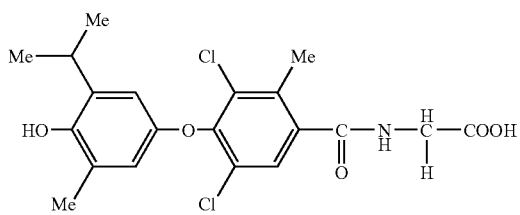

N-[3,5-Dibromo-2-methyl-4-(3-methyl-4-hydroxy-5-isopropylphenoxy)benzoyl]glycine (E8).

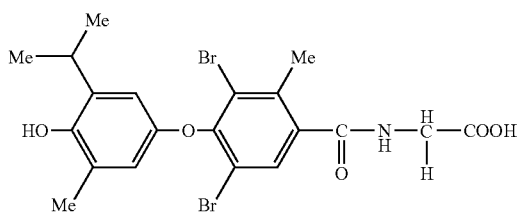

N-[3,5-Dimethyl-2-methyl-4-(3-methyl-4-hydroxy-5-isopropylphenoxy)benzoyl]glycine (E9).

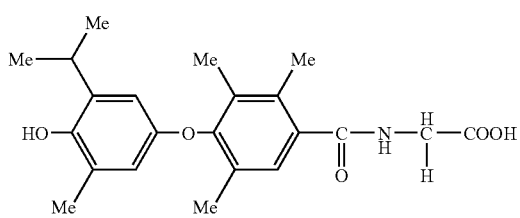

L-N-[3,5-Dibromo-4-(3-fluoro-4-hydroxy-5-isopropylphenoxy)phenylacetyl]valine (E10).

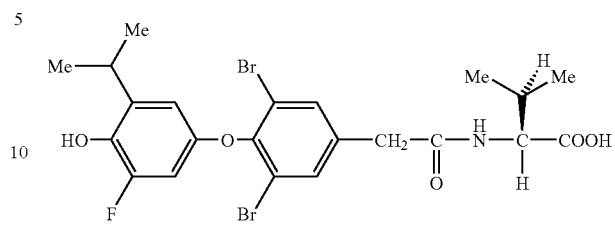

D-N-[3,5-Dibromo-4-(3-chloro-4-hydroxy-5-isopropylphenoxy)phenylacetyl]phenylglycine (E11)

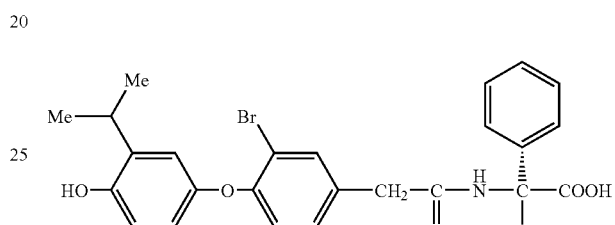

L-N-[3,5-Dibromo-4-(4-hydroxy-3-isopropyl-5-methylphenoxy)phenylacetyl]valine (E12)

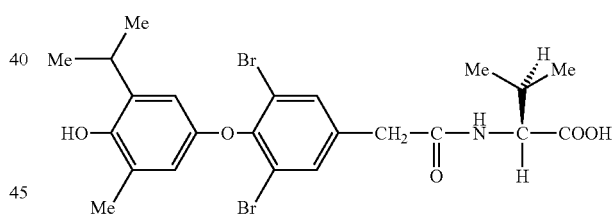

L-N-[3,5-Dibromo-4-(4-hydroxy-3-isopropyl-5-methylphenoxy)phenylacetyl]phenyl glycine (E13)

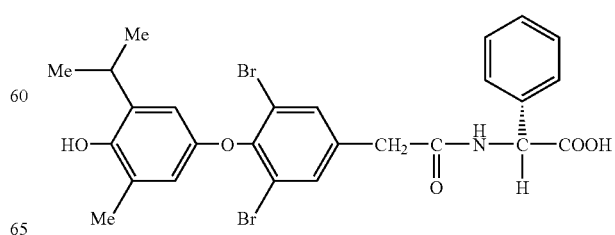

L-N-[3,5-Dibromo-4-(3,5-dimethyl-4-hydroxyphenoxy)phenylacetyl]phenylglycine (E14)

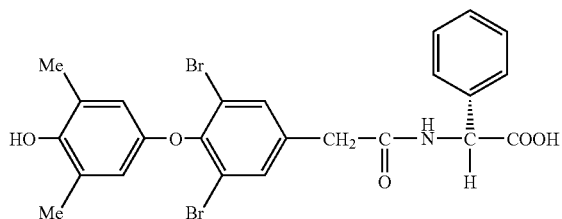

DETAILED DESCRIPTION OF THE INVENTION

The following definitions apply to the terms as used throughout this specification, unless otherwise limited in specific instances.

The term "thyroid receptor ligand" as used herein is intended to cover any moiety, which binds to a thyroid receptor. The ligand may act as an agonist, an antagonist, a partial agonist or a partial antagonist. Another term for "thyroid receptor ligand" is "thyromimetic".

Unless otherwise indicated, the term "alkyl" as employed herein alone or as part of another group includes both straight and branched chain hydrocarbons, containing 1 to 12 carbons (in the case of alkyl or alk), in the normal chain, preferably 1 to 4 carbons, such as methyl, ethyl, propyl, isopropyl, butyl, t-butyl, or isobutyl, pentyl, hexyl, isohexyl, heptyl, 4,4-dimethylpentyl, octyl, 2,2,4-trimethylpentyl, nonyl, decyl, undecyl, dodecyl. As defined and claimed herein, the term "alkyl" includes alkyl groups as defined above optionally substituted with 1 to 4 substituents which may halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, oxo, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, alkoxycarbonyl, alkylaminocarbonyl, nitro, cyano, thiol, haloalkyl, trihaloalkyl, alkylthio or carboxyl (or alkyl ester thereof).

Unless otherwise indicated, the term "cycloalkyl" as employed herein alone or as part of another group includes saturated cyclic hydrocarbon groups or partially unsaturated (containing 1 or 2 double bonds) cyclic hydrocarbon groups, containing one ring and a total of 3 to 8 carbons, preferably 3 to 6 carbons, forming the ring. As defined and claimed herein, the term "cycloalkyl" includes cycloalkyl groups as defined above optionally substituted with 1 or more substituents, such as those defined for alkyl.

The term "aryl" or "Ar" as employed herein alone or as part of another group refers to monocyclic and bicyclic aromatic groups containing 6 to 10 carbons in the ring portion (such as phenyl or naphthyl including 1-naphthyl and 2-naphthyl). As defined and claimed herein, the term "aryl" includes aryl groups as defined above optionally substituted through any available carbon atom(s) with 1 or more substituents, such as halo, alkyl, haloalkyl, alkoxy, haloalkoxy, alkenyl, trifluoromethyl, trifluoromethoxy, alkynyl, hydroxy, amino, nitro, cyano, carboxyl(or alkyl ester thereof) or any of the other substituents described for alkyl.

Unless otherwise indicated, the term "heteroaryl" or "heteroaromatic" as used herein alone or as part of another group refers to a 5- or 6-membered aromatic ring which includes 1, 2, 3 or 4 hetero atoms such as nitrogen, oxygen, or sulfur, and such rings fused to an aryl, cycloalkyl, heteroaryl or cycloheteroalkyl ring (e.g. benzothiophenyl, indole), and includes possible N-oxides. A "substituted heteroaryl" group includes a heteroaryl optionally substituted with one or more substituents such as any of the alkyl or aryl substituents set out above. As defined and claimed herein, the term "heteroaryl" includes heteroaryl groups as defined above optionally substituted through any available carbon atom(s) with 1 or more substituents, such as any of the substituents described for alkyl or aryl.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. As defined and claimed herein, the term "alkenyl" includes alkenyl groups as defined above optionally substituted through any available carbon atom(s) with 1 or more substituents, such as any of the substituents described for alkyl or aryl.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. As defined and claimed herein, the term "alkynyl" includes alkynyl groups as defined above optionally substituted through any available carbon atom(s) with 1 or more substituents, such as any of the substituents described for alkyl or aryl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cyclohexadienyl, and cycloheptadienyl, which may be optionally substituted as defined for cycloalkyl. As defined and claimed herein, the term "cycloalkenyl" includes cycloalkenyl groups as defined above optionally substituted through any available carbon atom(s) with 1 or more substituents, such as any of the substituents described for alkyl or aryl.

The term "halogen" or "halo" as used herein alone or as part of another group refers to chlorine, bromine, fluorine, and iodine as well as $CF_3$, with chlorine or bromine being preferred.

The term "alkanoyl" as employed herein alone or as part of another group is alkyl or cycloalkyl linked to a carbonyl group.

The term "aroyl" as employed herein alone or as part of another group is aryl or heteroaryl linked to a carbonyl group.

Unless otherwise indicated, the terms "alkoxy", "aryloxy" or "heteroaryloxy" as employed herein alone or as part of another group includes any of the above alkyl, aryl or heteroaryl groups linked thorough an oxygen atom.

The term "cyano," as used herein, refers to a —CN group.

The term "arylalkyl" and "heteroarylalkyl" as employed herein alone or as part of another group refer to alkyl groups as described above having an aryl or heteroaryl substituent. Representative examples of arylalkyl include, but are not limited to, benzyl, 2-phenylethyl, 3-phenylpropyl.

Unless otherwise indicated, the terms "arylalkoxy" and "cycloalkoxy" as employed herein alone or as part of another group include and aryl cycloalkyl groups linked thorough an oxygen atom.

The term "carboxylic acid" or "carboxyl", as used herein, refers to a —COOH group.

The term "benzyl" as used herein refers to —CH$_2$C$_6$H$_5$, which may optionally be substituted as defined above for alkyl.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C$_1$–C$_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tertbutyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts that are unsuitable for pharmaceutical uses but which can be employed, for example, for the isolation or purification of free compounds of formula I or their pharmaceutically acceptable salts, are also included. Preferred salts of the compounds of formula I which contain a basic group include monohydrochloride, hydrogensulfate, methanesulfonate, phosphate or nitrate. Preferred salts of the compounds of formula I which contain an acid group include sodium, potassium and magnesium salts and pharmaceutically acceptable organic amines.

The compounds of formula I may also have prodrug forms. Any compound that will be converted in vivo to provide the bioactive agent (i.e., the compound of formula I) is a prodrug within the scope and spirit of the invention.

Various forms of prodrugs are well known in the art. A comprehensive description of prodrugs and prodrug derivatives may be found in: (i) *The Practice of Medicinal Chemistry*, Camille G. Wermuth et al., Ch 31, (Academic Press, 1996); (ii) *Design of Prodrugs*, edited by H. Bundgaard, (Elsevier, 1985); and (iii) *A Textbook of Drug Design and Development*, P. Krogsgaard-Larson and H. Bundgaard, eds. Ch 5, pgs 113–191 (Harwood Academic Publishers, 1991). Said references are incorporated herein by reference.

Embodiments of prodrugs suitable for use in the present invention include lower alkyl esters, such as ethyl ester, or acyloxyalkyl esters such as pivaloyloxymethyl (POM) of a carboxylic acid group for R$_{13}$.

Embodiments of prodrugs suitable for use in the present invention include prodrugs which mask the free phenolic hydroxyl group present in formula I, as depicted in the structure below where the prodrug aroyl or alkanoyl group is the moiety, R—CO—, in which R is alkyl, heteroaryl or aryl.

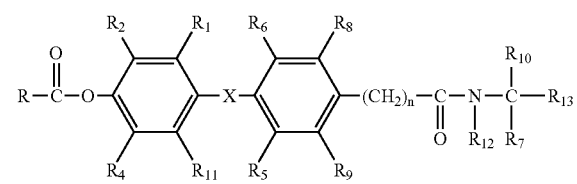

Furthermore, embodiments of prodrugs suitable for masking the phenolic hydroxyl group discussed above include phenolic alkyl ethers, such as depicted in the structure below where R=alkyl. Metabolic hydroxylation of the carbon of the alkyl group R that is attached to the phenolic oxygen leads to an intermediate capable of further decomposition to release the free phenol form of compounds of formula I.

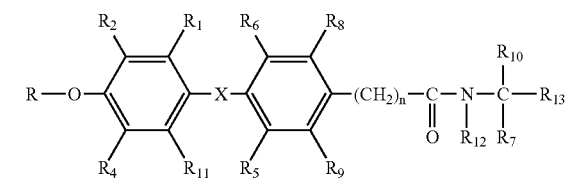

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The compounds of formula I may be prepared by the exemplary processes described in the following reaction schemes, as well as relevant published literature procedures that are used by one skilled in the art. Exemplary reagents and procedures for these reactions appear hereinafter and in the working Examples. Protection and deprotection in the Schemes below may be carried out by procedures generally known in the art (see, for example, T. W. Greene & P. G. M. Wuts, "Protecting Groups in Organic Synthesis", 3$^{rd}$ Edition, Wiley, 1999).

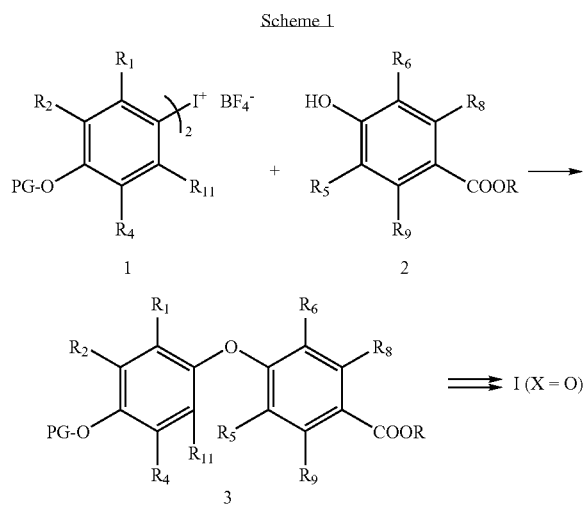

The iodonium salt methodology depicted in Scheme 1 is amply described in the literature for the synthesis of thyroid hormone analogs ("Novel Thyroid Receptor Ligands and Methods, Y.-L. Li, Y. Liu, A. Hedfors, J. Malm, C. Mellin, M. Zhang, PCT Int. App. WO 9900353 A1 990107; D. M. B. Hickey et al., J. Chem. Soc. Perkin Trans. 1, 3103–3111, 1988; N. Yokoyama et al., J. Med. Chem., 38, 695–707, 1995), and to diaryl ethers in general (E. A. Couladouros, V. I. Moutsos, Tetrahedron Lett., 40, 7023–7026, 1999). The reaction of an iodonium salt 1 with an appropriate hydroxy benzoic acid intermediate 2 provides the diaryl ether product 3 which may be readily converted by those of normal skill in the art to compounds of formula I in which X=O.

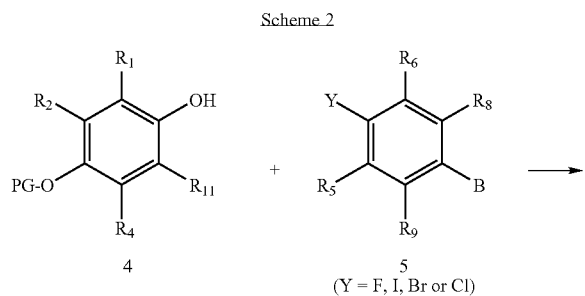

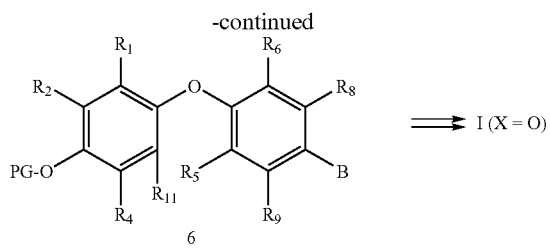

Scheme 2 depicts another general synthetic approach to compounds of formula I for which X=O. An appropriately substituted phenol 4 is alkylated with an appropriately substituted intermediate 5, in which Y is a displaceable group such as fluoro, chloro, iodo or bromo and the activating group B is one that both activates the group Y towards nucleophilic displacement and is capable of being subsequently transformed to a carboxylic acid (such as formyl (CHO) or nitro ($NO_2$), to provide the intermediate 6. The activating group B in intermediate 6 is then subsequently transformed to a carboxylic acid or derivative which can then be further converted to compounds of formula I for which X=O. Such activating functional groups and their means of conversion are well-known to those skilled in the art. For example, when B is a nitro function in intermediate 6, the nitro group can be reduced to an amino group by methods well known in the art, such as the use of catalytic hydrogenation in the presence of, for example, Raney nickel or palladium on charcoal catalyst, in a polar solvent such as glacial acetic acid or ethanol. Alternatively, the reduction can be accomplished using iron powder in aqueous glacial acetic acid at ambient temperatures. The resulting aryl amine can be converted to the corresponding diazonium salt by the use, for example, of a mixture of sodium nitrite and sulfuric acid in appropriate solvents. The resulting diazonium group can then be converted to a formyl group (CHO) by the reaction with carbon monoxide catalyzed by an appropriate palladium catalyst such as palladium acetate. After coupling to the intermediate 5, subsequent protecting group and functional group manipulation provides the desired compounds of formula I in which X=O. Another activating group is formyl (B=—CHO). After coupling to the second aromatic ring, the aldehyde group can be oxidized to a carboxylic acid, then converted to the compounds of formula I in which n=0. Furthermore, the same resulting carboxylic acid can be homologated to an acetic acid group by well known means such as the Arndt-Eistert homologation to ultimately provide examples of I for which n=1. The approach depicted in Scheme 2 for the general synthesis of diaryl ethers for thyromimetics is well precedented in the literature (P. D. Leeson, J. C. Emmett, J. Chem. Perkin Trans. I, 3085–3096, 1988; N. Yokoyama et al., J. Med. Chem., 38, 695–707, 1995).

Further means for synthesizing compounds of formula I in which X=O, NH, S, CO or $CH_2$ are generally described in the literature (for X=O: D. M. B. Hickey et al., J. Chem. Soc. Perkin Trans. I, 3097–3102, 1988; Z.-W. Guo et al., J. Org. Chem., 62, 6700–6701, 1997; D. M. T. Chan et al., Tetrahedron Lett., 39, 2933–2936, 1998; D. A. Evans et al., Tetrahedron Lett., 39, 2937–2940, 1998; G. M. Salamonczyk et al., Tetrahedron Lett., 38, 6965–6968, 1997; J.-F. Marcoux, J. Am. Chem. Soc., 119, 10539–10540, 1997; A. V. Kalinin et al., J. Org. Chem., 64, 2986–2987, 1999; for X=N: D. M. T. Chan et al., Tetrahedron Lett., 39, 2933–2936, 1998; J. P. Wolfe et al., J. Am. Chem. Soc., 118, 7215, 1996; M. S. Driver, J. F. Hartwig, J. Am. Chem. Soc., 118, 7217, 1996; see references in the review by C. G. Frost, P. Mendonca, J. Chem. Soc. Perkin I, 2615–2623, 1998; for X=S: C. R. Harrington, Biochem. J., 43, 434–437, 1948; A. Dibbo et al., J. Chem. Soc., 2890–2902, 1961; N. Yokoyama et al., U.S. Pat. No. 5,401,772, 1995; for X=CO or CH$_2$: L. Horner, H. H. G. Medem, Chem. Ber., 85, 520–530, 1952; G. Chiellini et al., Chemistry & Biology, 5, 299–306, 1998; and for X=CF2, see G. S. Lal et al., J. Org. Chem., 65, 4830–4832, 2000).

Methods applicable to the synthesis of compounds of formula I in which X=O and R$_2$ and R$_3$ are independently varied as hydrogen, halogen and alkyl are described in "Novel Thyroid Receptor Ligands and Methods, Y.-L. Li, Y. Liu, A. Hedfors, J. Malm, C. Mellin, M. Zhang, PCT Int. App. WO 9900353 A1 990107.

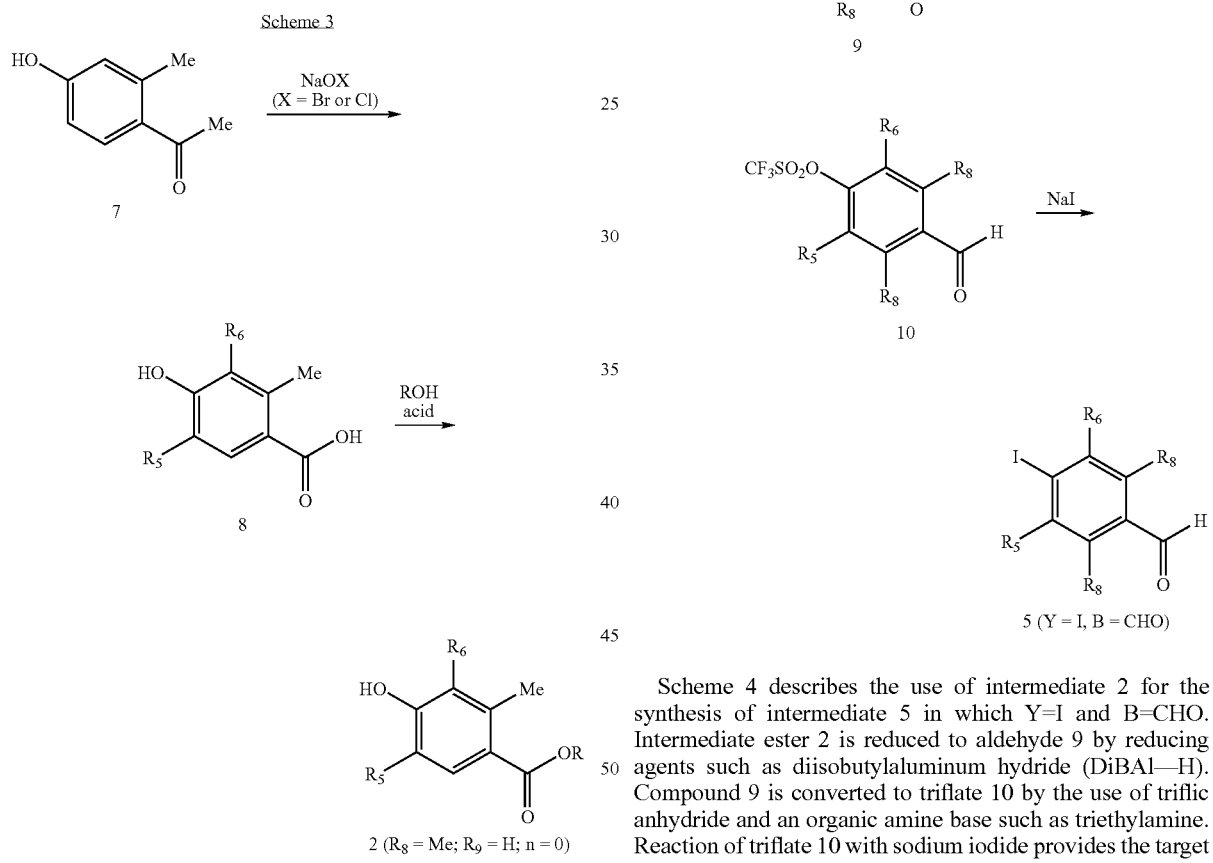

Scheme 3 describes the synthesis of intermediate 2 in which R$_5$=R$_6$=Br or Cl, R$_8$=Me, R$_9$=H, R=H and n=0. Acetophenone 7 (commercially available) is subjected to haloform reaction conditions with sodium hypochlorite or hypobromite to simultaneously convert the acetyl function to carboxyl and to halogenate the two positions ortho to the phenolic hydroxyl group. Esterification gives the target intermediate 2 which is employed in the chemistry described in Scheme 4.

Scheme 4 describes the use of intermediate 2 for the synthesis of intermediate 5 in which Y=I and B=CHO. Intermediate ester 2 is reduced to aldehyde 9 by reducing agents such as diisobutylaluminum hydride (DiBAl—H). Compound 9 is converted to triflate 10 by the use of triflic anhydride and an organic amine base such as triethylamine. Reaction of triflate 10 with sodium iodide provides the target aryl iodide aldehyde 5 which can be utilized in the chemistry described in Scheme 2 above.

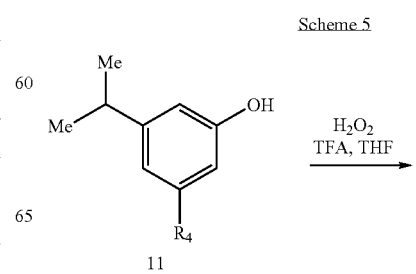

15

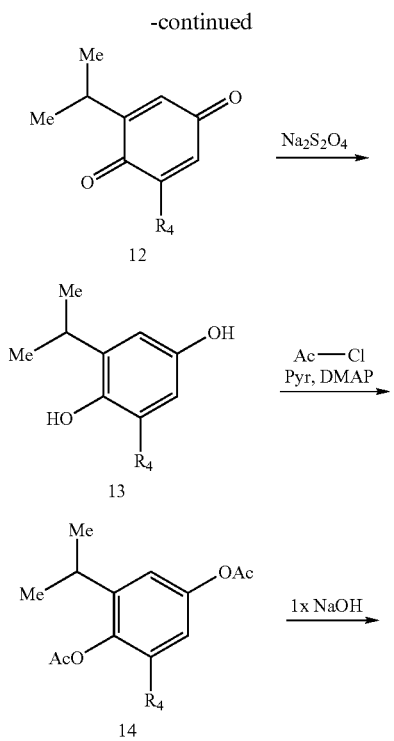

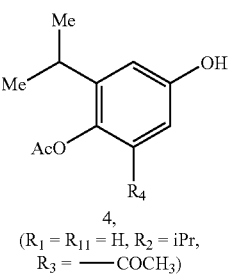

4,
($R_1 = R_{11} = H$, $R_2 = iPr$,
$R_3 = —COCH_3$)

Scheme 5 describes the synthesis of intermediate 4 in which $R_1$ and $R_{11}$=H, $R_2$=isopropyl and $R_3$ is an acetyl protecting group (—COCH$_3$). Phenol 11 is oxidized to quinone 12, which upon reduction with sodium hydrosulfite (Na$_2$S$_2$O$_4$) is converted to hydroquinone 13. Acetylation of 13 under standard conditions gives bis-acetate 14 which provides the desired target compound 4 after treatment with 1 equivalent of sodium hydroxide to remove the least hindered acetate group to provide the compound 4 which can be utilized in the chemistry described in Scheme 2 above.

Scheme 6

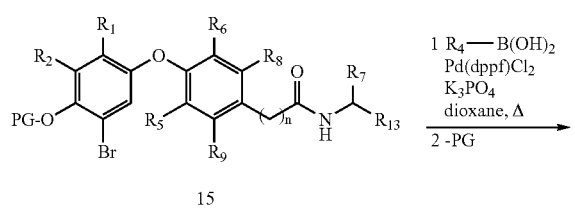

16

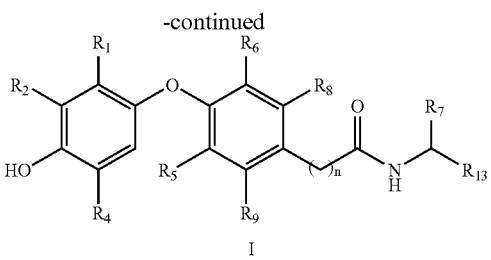

Scheme 6 describes an approach to the synthesis of compounds of formula I in which the group $R_4$ is a lower alkyl group, such as methyl or ethyl. Aryl bromide intermediate 15 is obtained by bromination of the corresponding free phenol ($R_3$=OH; obtained by procedures such as those described in Scheme 1 and Scheme 2), followed by installation of a protecting group (PG) on the phenolic hydroxyl. The group $R_4$ is introduced by coupling the aryl bromide intermediate 15 with an alkyl boronic acid in the presence of an appropriate palladium catalyst, such as [1,1'-bis(diphenylphosphino)ferrocene]dichloropalladium(II) (Harada et al, Synlett, 1995, 283). The aryl bromide intermediate 15 may be substituted by the corresponding aryl iodide or aryl triflate and undergo the same transformation.

Scheme 7

(7.1)

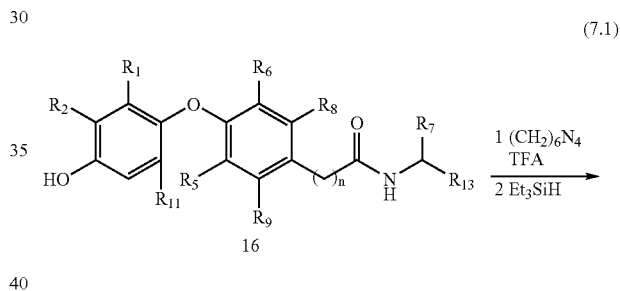

(7.2)

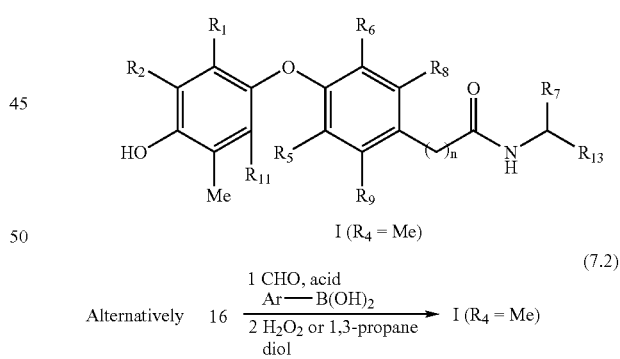

Scheme 7 depicts two procedures for the specific introduction of a methyl group in the $R_4$ position. Both methods proceed by (1) hydroxymethylation ortho to the phenolic hydroxyl group ($R_3$) in intermediate 16 (obtained by following procedures such as those described in Scheme 1 and Scheme 2, followed by (2) reduction of the hydroxymethyl group to a methyl group using a reagent such as triethylsilane. In reaction 7.1, hydroxymethylation is achieved by the use of hexamethylenetetramine in the presence of trifluoroacetic acid. In reaction 7.2, the hydroxymethylation step is promoted by the use of benzene boronic acid which complexes the initial adduct in the form of a dioxaborin intermediate. The desired hydroxymethyl compound is liberated either by exchange with ethylene glycol or reaction with hydrogen peroxide (Nagata et al, Synthesis, 1979, 365).

Other means are known to those of normal skill in the art for installing a methyl group on an aromatic ring. For example: (1) aryl bromides and iodides may be methylated by treatment with $Me_4Sn$ (tetramethyltin) in the presence of palladium catalyst (Tet Lett, 1999, 40, 2719–2722); (2) aryl triflates are methylated by treatment with $Me_3In$ (trimethylindium) in the presence of palladium catalyst (Org Lett, 1999, 1, 1267–1269; (3) aryl triflates are converted to aryl methyl compounds by treatment with $Me_3Al$ (trimethylaluminum) in the presence of palladium catalyst; (4) aryl triflates are also methylated by treatment with methyl boronic acid in the presence of palladium catalyst (Synlett, 1995, 283–284).

UTILITIES & COMBINATIONS

UTILITIES: The compounds of the present invention are thyroid receptor ligands, and include compounds that are, for example, selective agonists, partial agonists, antagonists or partial antagonists of the thyroid receptor. Preferably compounds of the present invention possess activity as agonists of the thyroid receptor, preferably selective agonists of the thyroid receptor-beta, and may be used in the treatment of diseases or disorders associated with thyroid receptor activity. In particular, compounds of the present invention may be used in the treatment of diseases or disorders associated with metabolism dysfunction or which are dependent upon the expression of a $T_3$ regulated gene.

Accordingly, the compounds of the present invention can be administered to mammals, preferably humans, for the treatment of a variety of conditions and disorders, including, but not limited to hypothyroidism; subclinical hyperthyroidism; non-toxic goiter; atherosclerosis; thyroid hormone replacement therapy (e.g., in the elderly); malignant tumor cells containing the thyroid receptor; papillary or follicular cancer; maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); accelerating healing of complicated fractures, e.g. distraction osteogenesis; in joint replacement; eating disorders (e.g., anorexia); treatment of obesity and growth retardation associated with obesity; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of hyperinsulinemia; stimulation of osteoblasts, bone remodeling and cartilage growth; regulation of food intake; treatment of insulin resistance, including NIDDM, in mammals (e.g., humans); treatment of insulin resistance in the heart; treatment of congestive heart failure; treatment of musculoskeletal impairment (e.g., in the elderly); improvement of the overall pulmonary function; skin disorders or diseases, such as glucocorticoid induced dermal atrophy, including restoration of dermal atrophy induced by topical glucocorticoids, and the prevention of dermal atrophy induced by topical glucocorticoids (such as the simultaneous treatment with topical glucocorticoid or a pharmacological product including both glucocorticoid and a compound of the invention), the restoration/prevention of dermal atrophy induced by systemic treatment with glucocorticoids, restoration/prevention of atrophy in the respiratory system induced by local treatment with glucocorticoids, UV-induced dermal atrophy, dermal atrophy induced by aging (wrinkles, etc.), wound healing, keloids, stria, cellulite, roughened skin, actinic skin damage, lichen planus, ichtyosis, acne, psoriasis, Dernier's disease, eczema, atopic dermatitis, chloracne, pityriasis and skin scarring.

The term treatment is also intended to include prophylactic treatment. In addition, the conditions, diseases, and maladies collectively referenced to as "Syndrome X" or Metabolic Syndrome as detailed in Johannsson *J. Clin. Endocrinol. Metab.*, 82, 727–34 (1997), may be treated employing the compounds of the invention.

COMBINATIONS: The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other modulators and/or ligands of the thyroid receptor or other suitable therapeutic agents useful in the treatment of the aforementioned disorders including: anti-diabetic agents; anti-osteoporosis agents; anti-obesity agents; growth promoting agents (including growth hormone secretagogues); anti-inflammatory agents; anti-anxiety agents; anti-depressants; anti-hypertensive agents; cardiac glycosides; cholesterol/lipid lowering agents; appetite suppressants; bone resorption inhibitors; thyroid mimetics (including other thyroid receptor agonists); anabolic agents; and anti-tumor agents.

Examples of suitable anti-diabetic agents for use in combination with the compounds of the present invention include biguanides (e.g., metformin or phenformin), glucosidase inhibitors (e.g. acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, SGLT2 inhibitors, glycogen phosphorylase inhibitors, inhibitors of fatty acid binding protein (aP2), glucagon-like peptide-1 (GLP-1), and dipeptidyl peptidase IV (DP4) inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-obesity agents for use in combination with the compounds of the present invention include aP2 inhibitors, PPAR gamma antagonists, PPAR delta agonists, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), other thyroid receptor beta drugs, such as a thyroid receptor ligand as disclosed in WO 97/21993 (U. Cal SF), WO 99/00353 (KaroBio) and GB98/284425 (KaroBio), CB-1 (cannabinoid receptor) antagonists (see G. Colombo et al, "Appetite Suppression and Weight Loss After the Cannabionid Antagonist SR 141716", Life Sciences, Vol 63, PL 113–117 (1998)) and/or an anorectic agent, such as dexamphetamine, phentermine, phenylpropanolamine or mazindol.

The compounds of the present invention may be combined with growth promoting agents, such as, but not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

The compounds of the invention may also be used in combination with growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotinin 5-$HT_D$ agonists, such as sumatriptan, or agents which inhibit somatostatin or its release, such as physostigmine and pyridostigmine. A still further use of the disclosed compounds of the invention is in combination with parathyroid hormone, PTH(1–34) or bisphosphonates, such as MK-217 (alendronate).

A still further use of the compounds of the invention is in combination with estrogen, testosterone, a selective estrogen receptor modulator, such as tamoxifen or raloxifene, or other androgen receptor modulators, such as those disclosed in Edwards, J. P. et al., *Bio. Med. Chem. Let.*, 9, 1003–1008 (1999) and Hamann, L. G. et al., *J. Med. Chem.*, 42, 210–212 (1999).

A further use of the compounds of this invention is in combination with steriodal or non-steroidal progesterone receptor agonists ("PRA"), such as levonorgestrel, medroxyprogesterone acetate (MPA).

Examples of suitable anti-inflammatory agents for use in combination with the compounds of the present invention include prednisone, dexamethasone, Enbrel®, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelmac® and Maxi-K® openers such as those disclosed in U.S. Pat. No. 6,184,231 B1).

Example of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

For the treatment of skin disorders or diseases as described above, the compounds of the present invention may be used alone or optionally in combination with a retinoid, such as tretinoin, or a vitamin D analog.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors, squalene synthetase inhibitors, fibrates, bile acid sequestrants, ACAT inhibitors, MTP inhibitors, lipooxygenase inhibitors, an ileal $Na^+$/bile acid cotransporter inhibitor, cholesterol absorption inhibitors, and cholesterol ester transfer protein inhibitors (e.g., CP-529414).

MTP inhibitors which may be employed herein in combination with one or more compounds of formula I include MTP inhibitors as disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440 all incorporated herein by reference.

A preferred MTP inhibitor is

9-[4-[4-[[2-(2,2,2-Trifluoroethoxy)benzoyl]amino]-1-piperidinyl]butyl]-N-(2,2,2-trifluoroethyl)-9H-fluorene-9-carboxamide:

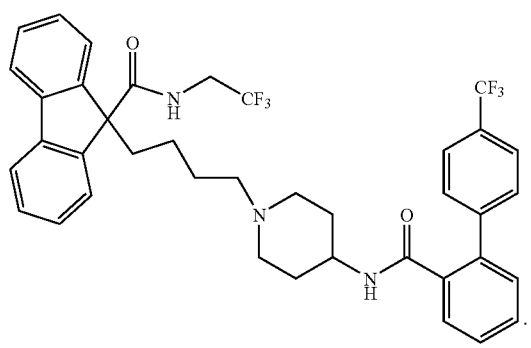

The HMG CoA reductase inhibitors which may be employed in combination with one or more compounds of formula I include mevastatin and related compounds as disclosed in U.S. Pat. No. 3,983,140, lovastatin (mevinolin) and related compounds as disclosed in U.S. Pat. No. 4,231, 938, pravastatin and related compounds such as disclosed in U.S. Pat. No. 4,346,227, simvastatin and related compounds as disclosed in U.S. Pat. Nos. 4,448,784 and 4,450,171.

Further HMG CoA reductase inhibitors which may be employed herein include fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pyrazole analogs of mevalonolactone derivatives as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No.0,142,146 A2, as well as other known HMG CoA reductase inhibitors.

The squalene synthetase inhibitors which may be used in combination with the compounds of the present invention include, but are not limited to, α-phosphonosulfonates disclosed in U.S. Pat. No. 5,712,396, those disclosed by Biller et al, J. Med. Chem., 1988, Vol. 31, No. 10, pp 1869–1871, including isoprenoid (phosphinylmethyl)phosphonates, terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, as well as other squalene synthetase inhibitors as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

Bile acid sequestrants which may be used in combination with the compounds of the present invention include cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives such as disclosed in U.S. Pat. No. 4,759,923, quaternary amine poly(diallyidimethylammonium chloride) and ionenes such as disclosed in U.S. Pat. No. 4,027,009, and other known serum cholesterol lowering agents.

ACAT inhibitors suitable for use in combination with compounds of the invention include ACAT inhibitors as described in, Drugs of the Future 24, 9–15 (1999), (Avasimibe); "The ACAT inhibitor, C1-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB 100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62.

Examples of suitable cholesterol absorption inhibitor for use in combination with the compounds of the invention include SCH48461 (Schering-Plough), as well as those disclosed in Atherosclerosis 115, 45–63 (1995) and J. Med. Chem. 41, 973 (1998).

Examples of suitable ileal $Na^+$/bile acid cotransporter inhibitors for use in combination with the compounds of the invention include compounds as disclosed in Drugs of the Future, 24, 425–430 (1999).

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone, TRH diethylstilbesterol, estrogens, β-agonists, theophylline, anabolic steroids, dehydroepiandrosterone, enkephalins, E-series prostagladins, retinoic acid and compounds as disclosed in U.S. Pat. No. 3,239,345, e.g., Zeranol®; U.S. Pat. No. 4,036,979, e.g., Sulbenox® or peptides as disclosed in U.S. Pat. No. 4,411,890.

The aforementioned patents and patent applications are incorporated herein by reference.

The above other therapeutic agents, when employed in combination with the compounds of the present invention, may be used, for example, in those amounts indicated in the Physicians' Desk Reference (PDR) or as otherwise determined by one of ordinary skill in the art.

Where the compounds of the invention are utilized in combination with one or more other therapeutic agent(s), either concurrently or sequentially, the following combination ratios and dosage ranges are preferred:

When combined with a hypolypidemic agent, an antidepressant, a bone resorption inhibitor and/or an appetite suppressant, the compounds of formula I may be employed in a weight ratio to the additional agent within the range from about 500:1 to about 0.005:1, preferably from about 300:1 to about 0.01:1.

Where the antidiabetic agent is a biguanide, the compounds of formula I may be employed in a weight ratio to biguanide within the range from about 0.01:1 to about 100:1, preferably from about 0.5:1 to about 2:1.

The compounds of formula I may be employed in a weight ratio to a glucosidase inhibitor within the range from about 0.01:1 to about 100:1, preferably from about 0.5:1 to about 50:1.

The compounds of formula I may be employed in a weight ratio to a sulfonylurea in the range from about 0.01:1 to about 100:1, preferably from about 0.2:1 to about 10:1.

The compounds of formula I may be employed in a weight ratio to a thiazolidinedione in an amount within the range from about 0.01:1 to about 100:1, preferably from about 0.5:1 to about 5:1. The thiazolidinedione may be employed in amounts within the range from about 0.01 to about 2000 mg/day, which may optionally be administered in single or divided doses of one to four times per day. Further, where the sulfonylurea and thiazolidinedione are to be administered orally in an amount of less than about 150 mg, these additional agents may be incorporated into a combined single tablet with a therapeutically effective amount of the compounds of formula I.

Metformin, or salt thereof, may be employed with the compounds of formula I in amounts within the range from about 500 to about 2000 mg per day, which may be administered in single or divided doses one to four times daily.

The compounds of formula I may be employed in a weight ratio to a PPAR-alpha agonist, a PPAR-gamma agonist, a PPAR-alpha/gamma dual agonist, an SGLT2 inhibitor and/or an aP2 inhibitor within the range from about 0.01:1 to about 100:1, preferably from about 0.5:1 to about 5:1.

An MTP inhibitor may be administered orally with the compounds of formula I in an amount within the range of from about 0.01 mg/kg to about 100 mg/kg and preferably from about 0.1 mg/kg to about 75 mg/kg, one to four times daily. A preferred oral dosage form, such as tablets or capsules, may contain the MTP inhibitor in an amount of from about 1 to about 500 mg, preferably from about 2 to about 400 mg, and more preferably from about 5 to about 250 mg, administered on a regimen of one to four times daily. For parenteral administration, the MTP inhibitor may be employed in an amount within the range of from about 0.005 mg/kg to about 10 mg/kg and preferably from about 0.005 mg/kg to about 8 mg/kg, administered on a regimen of one to four times daily.

A HMG CoA reductase inhibitor may be administered orally with the compounds of formula I within the range of from about 1 to 2000 mg, and preferably from about 4 to about 200 mg. A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A squalene synthetase inhibitor may be administered with the compounds of formula I within the range of from about 10 mg to about 2000 mg and preferably from about 25 mg to about 200 mg. A preferred oral dosage form, such as tablets or capsules, will contain the squalene synthetase inhibitor in an amount of from about 10 to about 500 mg, preferably from about 25 to about 200 mg.

The compounds of formula I of the invention can be administered orally or parenterally, such as subcutaneously or intravenously, as well as by nasal application, rectally or sublingually to various mammalian species known to be subject to such maladies, e.g., humans, in an effective amount within the dosage range of abut 0.01 μg/kg to about 1000 μg/kg, preferably about 0.1 μg/kg to 100 μg/kg, more preferably about 0.2 μg/kg to about 50 μg/kg (or form about 0.5 to 2500 mg, preferably from about 1 to 2000 mg) in a regimen of single, two or four divided daily doses.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

EXAMPLES

The following Examples represent preferred embodiments of the present invention. However, they should not be construed as limiting the invention in any way. The $^1$H NMR spectra were consistent with the assigned structures. Mass spectra were recorded on a Perkin-Elmer, API 150Ex spectrometer, with turbo "ion spray" on negative ion mode (ES−1) or positive (ES+1), using a Zorbax SB-C8 column (LC-MS). Appropriate procedures for the preparation of methyl[3,5-chloro-4-(4-methoxy-3-isopropylphenoxy)]benzoate and methyl-N-[3,5-dichloro-4-(4-methoxy-3-isopropylphenoxy)benzoyl]glycine can be found in: "Novel Thyroid Receptor Ligands and Methods." Li, Y.-L.; Liu, Y.; Hedfors, A.; Malm, J.; Mellin, C.; Zhang, M. WO99/00353, PCT/EP98/04039 and "Novel diphenyl ether derivatives which are thyroid hormone beta-receptor ligands useful for treating metabolic disorders." Hangeland, J.; Zhang, M.; Caringal, Y.; Ryono, D.; Li, Y.-L.; Malm, J.; Liu, Y.; Garg, N.; Litten, C.; Garcia Collazo, A. M.; Koehler, K. WO00/039077, PCT/IB99/02084, respectively. Procedures for the preparation of 3,5-dichloro-2-methyl-4-(4-hydroxy-3-isopropylphenoxy)-benzoic acid can be found in "Benzamide ligands for the thyroid receptor". Ryono, Denis E. WO01/94293, U.S. Pat. No. 6,395,784.

Example 1

N-[3,5-Dichloro-4-(4-hydroxy-3-isopropyl-5-methylphenoxy)benzoyl]glycine (E1)

(a) Nitric acid (2.84 mL, 65%) was added to a stirred solution of methyl[3,5-dichloro-4-(3-isopropyl-4-methoxyphenoxy)]benzoate (2.84 g, 7.64 mmol) in benzene (200 mL). The resulting yellow reaction mixture was stirred at room temperature for three hours and then poured out in sodium hydrogencarbonate (saturated solution). The resulting organic and aqueous phases was separated and the aqueous phase was extracted with ethyl acetate. The combined organic phases was dried over sodium sulfate and concentrated to give 2.40 g of a light yellow solid. The solid was solved in ethanol (150 mL, 95.5%), sodium dithionite (Na$_2$S$_2$O$_4$, 85% purity, 7.12 g, 35.0 mmol) was added and the reaction mixture heated to reflux. After 16 hours, a second batch of sodium dithionite (3.00 g, 14.7 mmol) was added to the reaction mixture. After three hours, the reaction mixture was cooled down to room temperature, neutralized with sodium hydrogencarbonate (saturated solution) and concentrated. The residue was diluted with ethyl acetate (75 mL) and washed with water (50 mL). The organic phase was dried over anhydrous sodium sulfate and concentrated to give a light yellow solid. The yellow solid was filtered through a short plug of silica, to give 2.2 g (75%) of methyl[3,5-dichloro-4-(3-amino-5-isopropyl-4-methoxyphenoxy)]benzoate.

(b) A solution of sodium nitrite (0.30 g, 13 mmol) in water (5 mL) was added to a vigorously stirred mixture of methyl [3,5-dichloro-4-(3-amino-5-isopropyl-4-methoxyphenoxy)]benzoate (1.1 g, 2.86 mmol), methanol (100 mL) and hydrochloric acid (75 mL, 37%). The reaction mixture was stirred for one hour and then a solution of potassium iodide (1.43 g, 8.6 mmol) in water (5 mL) was added and the reaction mixture was stirred for 30 minutes. The temperature was kept at 0° C. inside the flask during the whole course of reaction. After attaining room temperature the brownish reaction mixture was extracted with chloroform (3×50 mL), the combined organic phases washed with sodium hydrogensulphate (saturated solution) followed by sodium thiosulphate (saturated solution). The organic phase was concentrated to give a dark red oily residue which was purified on column (silica gel, n-heptane/ethyl acetate 95:5), to give 0.78 g (71%) of methyl[3,5-dichloro-4-(3-iodo-5-isopropyl-4-methoxyphenoxy)]benzoate as a pale yellow mass.

(c) Methyl[3,5-dichloro-4-(3-iodo-5-isopropyl-4-methoxyphenoxy)]benzoate (0.500 mg, 1.01 mmol), tripotassium phosphate (1.07 g, 5.05 mmol), methyl boronic acid (0.303 mg, 5.05 mmol) and dioxane was mixed in a Schlenk tube under nitrogen gas. PdCl$_2$(dppf) was added to the tube under nitrogen gas and the reaction mixture was heated at 100° C. for 16 hours. The reaction mixture was filtered through a short pad of silica and concentraded. The dark residue was purified on column (silica gel, n-heptane/ethyl acetate 95:5) to give a 85:15 mixture of methyl[3,5-dichloro-4-(3-isopropyl-4-methoxy-5-methylphenoxy)]benzoate and methyl[3,5-dichloro-4-(3-isopropyl-4-methoxyphenoxy)]benzoate. The mixture was obtained as a white solid mass (0.250 mg, 55%) and was used without further purification in the next step.

(d) The mixture of methyl[3,5-dichloro-4-(3-isopropyl-4-methoxy-5-methylphenoxy)]benzoate and methyl[3,5-dichloro-4-(3-isopropyl-4-methoxyphenoxy)]benzoate above (250 mg) was solved in tetrahydrofuran (15 mL) and lithium hydroxide (1 N, 15 mL) was added. After 90 minutes stirring at room temperature, the reaction mixture was acidified with hydrochloride (1 N) and the aqueous and organic phase separated. The organic phase was dried over sodium sulfate and concentrated to give 0.250 g of a white solid mass, which was mixed with glycine methyl ester (164 mg, 1.30 mmol), 3-ethyl-1-[3-(dimethylamino)-propyl]carbodiimide hydrochloride (EDCI) (118 mg, 0.978 mmol) and N,N-dimethyl-formamide (20 mL). The reaction mixture was stirred for 10 minutes at room temperature, whereafter and 1-hydroxybenzotriazole hydrate (HOBt) (150 mg, 0.978 mmol) and triethyl-amine (0.272 mL, 1.96 mmol) was added. After 48 hours at room temperature, the reaction mixture was poured out in water (150 mL) and neutralized with sodium hydrogencarbonate. The aqueous phase was extracted with ethyl acetate (4×100 mL), the collected organic phases dried over magnesium sulfate and concentrated. The residue was purified on column (silica gel, gradient elution: n-heptane/ethyl acetate from 7:3 to 5:5). This gave 165 mg (60%) of methyl-N-[3,5-dichloro-4-(5-isopropyl-4-methoxy-3-methylphenoxy)benzoyl]glycine as a white solid mass.

(e) Boron trifluoride dimethyl sulfide (1.48 mL, 13.7 mmol) was added at 4° C. to a stirred solution of methyl-N-[3,5-dichloro-4-(5-isopropyl-4-methoxy-3-methylphenoxy)benzoyl]glycine (155 mg, 0.352 mmol) and dichloromethane (15 mL). The reaction mixture was stirred at room temperature for 24 hours and then treated with ice-water (30 mL), extracted with ethyl acetate and concentrated. The residue was purified on column (MPLC, silica gel, chloroform/methanol/acetic acid, gradient elution from 1/0/0 to 95/5/0.5) to give 110 mg (76%) of N-[3,5-dichloro-4-(4-hydroxy-3-isopropyl-5-methylphenoxy)benzoyl]glycine. LC-MS (ES−1): m/z 410.

Example 2

N-[3,5-Dichloro-4-(3-bromo-4-hydroxy-5-isopropylphenoxy)benzoyl]glycine (E2)

(a) Borontribromide (1 N, in dichloromethane) was added to a solution of methyl-N-[3,5-dichloro-4-(4-methoxy-3-isopropylphenoxy)benzoyl]glycine (114 mg, 0.267 mmol) in dichloromethane (5 mL) at −78° C. The resulting brown reaction mixture was left at −25° C. for 16 hours and at 4° C. for two hours. A mixture of methanol (5 mL) and water (5 mL) was added at −70° C., the reaction mixture concentrated and diluted with ethyl acetate. The organic phase was washed with water, dried over sodium sulfate and concentrated. This gave 107 mg of methyl-N-[3,5-dichloro-4-(4-hydroxy-3-isopropylphenoxy)benzoyl]glycine as a beige solid mass.

(b) Bromine (33 μL) was added dropwise to a well stirred mixture of methyl-N-[3,5-dichloro-4-(4-hydroxy-3-isopropylphenoxy)benzoyl]glycine (240 mg, 0.582 mmol), acetic acid (4 mL), sodium acetate (88 mg, 0.64 mmol) and a few drops of water. The reaction mixture was stirred at room temperature for 16 hours, sodium thiosulfate (saturated) was added and the yellow mixture concentrated. The residue was diluted with ethyl acetate and washed with water. The aqueous phase was extracted with dichloromethane, the combined organic phases washed with brine and dried over sodium sulfate. After concentration, 330 mg of a yellow sodid was obtained that was purified on column (silica gel, n-heptane/ethyl acetate, gradient elution from 100% n-heptane to a mixture of 20% n-heptane and 80% ethyl acetate). This gave 200 mg (70%) of methyl-N-[3,5-dichloro-4-(3-bromo-4-hydroxy-5-isopropylphenoxy)benzoyl]glycine as a white solid mass.

(c) Lithium hydroxide (1 N, 9 mL) was added at room temperature to a mixture of methyl-N-[3,5-dichloro-4-(3-bromo-4-hydroxy-5-isopropylphenoxy)benzoyl]glycine (150 mg, 0.305 mmol) and tetrahydrofuran (9 mL). After 16 hours, the reaction mixture was acidified with hydrochloric acid (1 N) and extracted with ethyl acetate. Filtration through a pad of silica gave N-[3,5-dichloro-4-(3-bromo-4-hydroxy-5-isopropylphenoxy)benzoyl]-glycine in quantitative yield as a light yellow solid. LC-MS (ES−1): m/z 476.

Example 3

N-[3,5-Dichloro-4-(2-bromo-4-hydroxy-5-isopropylphenoxy)benzoyl]glycine (E3)

(a) Bromine (13 μL, 0.26 mmol) was added dropwise to a well stirred mixture of methyl-N-[3,5-dichloro-4-(4-methoxy-3-isopropylphenoxy)benzoyl]glycine (50 mg, 0.12 mmol), acetic acid (1.0 mL), sodium acetate (35 mg, 0.26 mmol) and a few drops of water. The reaction mixture was stirred at room temperature for three hours, heated at 40° C. for 90 minutes and finally left at room temperature for 16 hours. Sodium acetate (17 mg) and bromine (6 μL) was added and the reaction mixture heated to 40° C. for two hours. The reaction mixture was left at 4° C. for three days. Sodium thiosulfate (saturated) was added and the yellow mixture concentrated. The residue was diluted with ethyl acetate and washed with water. The aqueous phase was extracted with dichloromethane, the combined organic phases washed with brine and dried over sodium sulfate. After concentration, the residue was purified on column (hplc, C$_8$, acetonitrile/water/formic acid, gradient elution from 20/80/0.5 to 100/0/0) to give 1.0 mg (2%) of methyl-N-[3,5-dichloro-4-(2-bromo-4-methoxy-5-isopropylphenoxy)benzoyl]glycine.

(b) Boron trifluoride dimethyl sulfide (10 μL, 80 μmol) was added at room temperature to a stirred solution of methyl-N-[3,5-dichloro-4-(2-bromo-4-methoxy-5-isopropylphenoxy)benzoyl]glycine (1.0 mg, 2.0 μmol) and dichloromethane (0.50 mL). The reaction mixture was stirred at room temperature for 8 hours and then treated with ice-water, extracted with ethyl acetate and washed with water. The organic phase was dried over sodium sulphate and concentrated to give a light yellow solid. The solid was purified on column (MPLC, silica gel, chloroform/methanol/acetic acid, gradient elution from 1/0/0 to 95/5/0.5) to give 0.90 mg (94%) of N-[3,5-dichloro-4-(2-bromo-4-hydroxy-5-isopropylphenoxy)benzoyl]glycine. LC-MS (ES−1): m/z 476.

Example 4

N-[3,5-Dichloro-4-(3-chloro-4-hydroxy-5-isopropylphenoxy)benzoyl]glycine (E4)

(a) Methyl[3,5-dichloro-4-(3-isopropyl-4-methoxyphenoxy)]benzoate (664 mg, 1.8 mmol) dissolved in acetone (40 mL), was added during 5 minutes at 0° C. to a stirred mixture of calcium hypochlorite (515 mg, 3.6 mmol), water (10 mL) and acetic acid (4 mL). The reaction mixture was stirred at 0° C. for 30 minutes and then 30 minutes at room temperature. The reaction mixture was poured out in water, extracted with ethyl acetate (3×50 mL), the combined organic phases washed with water (4×30 mL) and concentrated. The residue was purified on column (silica gel, n-heptane/ethyl acetate, gradient elution from 98:2 to 90:10) to give 240 mg (60%) of methyl[3,5-dichloro-4-(3-chloro-5-isopropyl-4-methoxyphenoxy)]benzoate. The calcium hypochlorite used in this step could be exchanged to t-butyl hypochlorite.

(b) Methyl[3,5-dichloro-4-(3-chloro-5-isopropyl-4-methoxyphenoxy)]benzoate, methanol (25 mL) and sodium hydroxide (6 N, 4 mL) was stirred at room temperature for 8 hours. The reaction mixture was neutralized with aqueous hydrochloric acid and extracted with ethyl acetate (3×30 mL). The combined organic phases were washed with water, concentrated and the residue titurated with n-heptane. This gave 133 mg (58%) of 3,5-dichloro-4-(3-chloro-5-isopropyl-4-methoxyphenoxy)benzoic acid obtained as a white solid.

(c) Glycine methyl ester hydrochloride (83 mg, 0.66 mmol) and triethylamine (100 mg, 0.99 mmol) was added to a stirred mixture of 3,5-dichloro-4-(3-chloro-5-isopropyl-4-methoxyphenoxy)benzoic acid (130 mg, 0.33 mmol), EDCI (88 mg, 0.46 mmol), HOBt (86 mg, 0.56 mmol) and N,N-dimethylformamide (15 mL). The reaction mixture was stirred for 48 hours at room temperature, poured out in a mixture of hydrochloric acid (1 N, 5.0 mL) and water (50 mL), and extracted with ethyl acetate (4×20 mL). The collected organic phases dried was washed with water (4×15 mL), the organic phase concentrated and the residue purified on column (silica gel, n-heptane/ethyl acetate, gradient elution from 90:10 to 75:25). This gave 90 mg (59%) of methyl-N-[3,5-dichloro-4-(3-chloro-5-isopropyl-4-methoxy-phenoxy)benzoyl]glycine.

(d) Boron trifluoride dimethyl sulfide (1.0 mL) was added at room temperature to a stirred solution of methyl-N-[3,5-dichloro-4-(3-chloro-5-isopropyl-4-methoxyphenoxy)benzoyl]glycine (90 mg) and dichloromethane (10 mL). The reaction mixture was stirred at room temperature for 24 hours, poured out in water and extracted with ethyl acetate (3×30 mL). The combined organic phases were washed with water (4×20 mL), concentrated and the resulting residue purified on column (silica gel, chloroform/methanol/acetic acid 94:6:0.65). This gave 53 mg (63%) of N-[3,5-dichloro-4-(3-chloro-4-hydroxy-5-isopropylphenoxy)benzoyl]glycine. LC-MS (ES+1): m/z 434.

Example 5

N-[3,5-Dichloro-4-(3-cyano-4-hydroxy-5-isopropylphenoxy)benzoyl]glycine (E5)

(a) Methyl[3,5-dichloro-4-(3-iodo-5-isopropyl-4-methoxyphenoxy)]benzoate (for preparation see ex. 1 a–b) (200 mg, 0.40 mmol), copper cyanide (50 mg, 0.56 mmol) and DMF (4 ml) was heated to 120° C. for 16 h. After attaining room temperature, the dark reaction mixture was quenched by saturated sodium hydrogencarbonate solution and extracted with ethyl acetate. The organic phase was dried over sodium sulfate and concentrated. The residue was purified on column (MPLC, silica gel, gradient elution: n-heptane/ethyl acetate from 1:0 to 9:1) to give 65 mg (41%) of methyl[3,5-dichloro-4-(3-cyano-5-isopropyl-4-methoxyphenoxy)]benzoate.

(b) Boron tribromide (1 N in dichloromethane, 0.93 mL) was added to a solution of methyl[3,5-dichloro-4-(3-cyano-5-isopropyl-4-methoxyphenoxy)]benzoate (32 mg, 81 µmol) in dichloromethane (0.75 mL) at −78° C. After 20 h at −25° C. and 16 h at room temperature, the reaction mixture was quenched by ice water at 0° C. and the organic solvent was removed by evaporation. The residue was acidified by hydrochloric acid (1 N) and extracted by ethyl acetate. The organic phase was dried over sodium sulfate and filtrated through a pad of silica. The resulting yellow solid was mixed with glycine methyl ester (23 mg, 0.18 mmol), EDCI (35 mg, 0.18 mmol) and N,N-dimethylformamide (1 mL). The reaction mixture was stirred for 10 minutes at room temperature, where after HOBt (28 mg, 0.18 mmol) and triethylamine (38 µL, 0.27 mmol) was added. After 16 hours at room temperature, the reaction mixture was poured out in water (5 mL) and neutralized with sodium hydrogencarbonate. The aqueous phase was extracted with ethyl acetate (2×10 mL) and the collected organic phases was dried over sodium sulfate and concentrated. The residue was purified on column (MPLC, silica gel, gradient elution: n-heptane/ethyl acetate from 9:1 to 7:3). This gave 15 mg (42%) of methyl-N-[3,5-dichloro-4-(3-cyano-4-hydroxy-5-isopropylphenoxy)benzoyl]glycine as a white solid mass.

(c) Boron tribromide (1 N in dichloromethane, 0.11 mL) was added to a solution of methyl-N-[3,5-dichloro-4-(3-cyano-4-hydroxy-5-isopropylphenoxy)benzoyl]glycine (7 mg, 16 µmol) in dichloromethane (0.5 mL) at −78° C. The resulting reaction mixture was stirred at room temperature for 16 h and thereafter quenched by ice water. The organic solvent was removed with evaporation and the remaining residue was acidified by hydrochloric acid (1 N) and extracted by ethyl acetate. Drying over sodium sulfate, concentration and purification on a silica SPE column (0.5 g, 3 mL, gradient elution: chloroform/methanol/acetic acid from 1:0:0 to 98:2:0.5) gave 3 mg (44%) of N-[3,5-dichloro-4-(3-cyano-4-hydroxy-5-isopropyl-phenoxy)benzoyl]glycine. LC-MS (ES−1): m/z 421.

Example 6

N-[3,5-Dichloro-4-(3-fluoro-4-hydroxy-5-isopropylphenoxy)benzoyl]glycine (E6)

(a) To a solution of methyl[3,5-dichloro-4-(3-isopropyl-4-methoxyphenoxy)]benzoate (2.0 g, 5.4 mmol) in benzene (200 ml), nitric acid (2.07 ml, 65%) was added drop wise. The mixture was further stirred for 1 h at room temperature. The reaction was monitored by TLC (65:35 n-heptane/ethyl acetate) and the mixture was quenched with saturated aqueous solution of sodium hydrogencarbonate. The resulting organic and aqueous phases were separated and the aqueous phase was extracted with ethyl acetate. The combined organic phase was washed with water, brine, and the organic phase was dried over magnesium sulfate, and concentrated. The crude product was crystallize from methanol to give 1.8 g, (80%) of methyl[3,5-dichloro-4(5-isopropyl-4-methoxy-3-nitrophenoxy)]benzoate.

(b) To the solution of methyl[3,5-dichloro-4-(5-isopropyl-4-methoxy-3-nitrophenoxy)]benzoate (500 mg, 1.21 mmol) in tetrahydrofuran (10 mL), lithium hydroxide (5 mL, 1M) was added. The mixture was stirred over night at room temperature. The reaction mixture was acidified with hydrochloric acid (1 N) and the aqueous and organic phase separated. The aqueous phase extracted with ethyl acetate. The combined organic phase was washed with water and dried over magnesium sulfate and concentrated. The crude product was purified on column (silica gel, chloroform/methanol/acetic acid 98:2:0.3) to give 418 mg (86%) of 3,5-dichloro-4-(5-isopropyl-4-methoxy-3-nitrophenoxy)benzoic acid.

(c) Glycine methyl ester hydrochloride (262 mg, 2.08 mmol) and triethylamine (317 mg, 3.13 mmol) was added to a stirred mixture of 3,5-dichloro-4-(5-isopropyl-4-methoxy-3-nitrophenoxy)]benzoic acid (418 mg, 1.04 mmol)), EDCI (401 mg, 2.08 mmol), HOBt (320 mg, 2.08 mmol) in N,N-dimethylformamide (50 mL). The reaction mixture was stirred for 24 hours at room temperature, poured out in a mixture of hydrochloric acid (1 N, 10 mL) and water (50 mL), and extracted with ethyl acetate. The collected organic phases dried was washed with water, the organic phase concentrated and the residue was purified on column (silica gel, n-heptane/ethyl acetate, gradient elution from 98:2 to 60:40) to give 380 mg (78%) of methyl-N-[3,5-dichloro-4-(5-isopropyl-4-methoxy-3-nitro-phenoxy)benzoyl]glycine.

(d) A mixture of methyl-N-[3,5-dichloro-4-(5-isopropyl-4-methoxy-3-nitro-phenoxy)benzoyl]glycine (380 mg, 0.81 mmol) and PtO$_2$ (40 mg) in ethyl acetate (10 mL) was stirred at room temperature under hydrogen (atmospheric pressure) for 24 h. Pt catalyst was removed by filtration through celite and the filtrate was concentrated, which was purified on column (silica gel, n-heptane/ethyl acetate, gradient elution from 98:2 to 60:40) to give 320 mg (89%) of methyl-N-[3,5-dichloro-4-(3-amino-5-isopropyl-4-methoxyphenoxy)benzoyl]glycine.

(e) A solution of nitrosonium tetrafluoroborate (55 mg, 0.47 mmol) in dichloromethane (5 mL) was cooled to 0° C. and methyl-N-[3,5-dichloro-4-(3-amino-5-isopropyl-4-methoxyphenoxy)benzoyl]glycine (189 mg, 0.43 mmol) was added. The reaction mixture was further stirred at 0° C. for 1 h. Dichloromethane was removed from nitrogen and o-xylene (10 mL) was added to the reaction mixture. The reaction mixture was refluxed for 1 h and the solvent was removed. The crude reaction mixture was purified on column (silica gel, n-heptane/ethyl acetate, gradient elution from 98:2 to 60:40) to give 50 mg (26%) of methyl-N-[3,5-dichloro-4-(3-fluro-5-isopropyl-4-methoxyphenoxy)benzoyl]glycine.

(f) Boron trifluoride dimethyl sulfide (2.0 mL) was added at room temperature to a stirred solution of methyl-N-[3,5-dichloro-4-(3-fluoro-5-isopropyl-4-methoxyphenoxy)benzoyl]glycine (50 mg, 0.11 mmol) and dichloromethane (8 mL). The reaction mixture was stirred at room temperature for 24 hours, poured out in water and extracted with ethyl acetate. The combined organic phases were washed with water, concentrated and the resulting residue purified on column (HPLC, ACE-$C_8$, acetonitrile/0.05% formic acid in water, gradient elution from 5/95 to 60/40) to give 5 mg (20%) of N-[3,5-dichloro-4-(3-fluoro-4-hydroxy-5-isopropylphenoxy)benzoyl]glycine. LC-MS (ES−1): m/z 414.

Example 7

N-[3,5-Dichloro-2-methyl-4-(4-hydroxy-3-isopropyl-5-methylphenoxy)-2-methyl-benzoyl]glycine (E7)

(a) A suspension of benzyltrimethylamonium tribromide (2.2 g, 5.63 mmol) and $CaCO_3$ (0.28 g, 2.82 mmol) was stirred for 2 hr at 20° C. in a 1:1 MeOH/$CH_2Cl_2$ solution (10 mL) containing 3,5-dichloro-2-methyl-4-(4-hydroxy-3-isopropylphenoxy)-benzoic acid (1.0 g, 2.82 mmol). Once HPLC analysis indicated that conversion to the desired monobrominated phenol was optimal, the reaction was quenched by addition of 15 mL of 1N HCl. After removal of the organic solvents under vacuum using a rotary evaporator, the aqueous suspension was extracted twice with EtOAc. After drying the combined EtOAc layers over $MgSO_4$, the salts were filtered prior to removal of the EtOAc under vacuum. The resulting residue after purification by gradient elution from a reverse phase C18 column employing MeOH/$H_2O$ containing 0.1% TFA yielded 3,5-dichloro-2-methyl-4-(3-bromo-4-hydroxy-5-isopropylphenoxy)benzoic acid (400 mg).

(b) HCl gas was bubbled through a solution of 3,5-dichloro-2-methyl-4-(3-bromo-4-hydroxy-5-isopropylphenoxy)benzoic acid (375 mg, 0.86 mmol) in MeOH (20 mL) for 5 min. Upon stirring at 20° C. for 22 hr, HPLC analysis revealed esterification was complete. After removal of the solvent under vacuum and dissolution of the residue in EtOAc, the EtOAc layer was washed 2× with $H_2O$ then with brine prior to drying over $MgSO_4$. Removal of the volatiles yielded 391 mg of crude methyl 3,5-dichloro-2-methyl-4-(3-bromo-4-hydroxy-5-isopropylphenoxy)benzoate as a brown solid which was not further purified.

(c) A stirred suspension of powdered anhydrous $K_3PO_4$ (473 mg, 2.23 mmol) and methylboronic acid (133 mg, 2.23 mmol) in a dioxane solution (5 mL) containing methyl 3,5-dichloro-2-methyl-4-(3-bromo-4-hydroxy-5-isopropylphenoxy)benzoate (263 mg, 0.59 mmol) was flushed with Ar for 15 min prior to addition of Pd(dppf)$Cl_2$ (168 mg, 0.21 mmol). After refluxing for 3 hr, the reaction was cooled, diluted with EtOAc, and filtered. The residue remaining after removal of the volatiles was chromatographed on silica gel. Progressive elution with 1:1 and then 3:1 $CH_2Cl_2$/hexane eluted 125 mg of methyl 3,5-dichloro-2-methyl-4-(3-methyl-4-hydroxy-5-isopropylphenoxy)benzoate as an orange foam.

(d) A solution of methyl 3,5-dichloro-2-methyl-4-(3-methyl-4-hydroxy-5-isopropylphenoxy)benzoate (125 mg, 0.33 mmol) and LiOH $H_2O$ (68 mg, 1.63 mmol) in a 5:1 THF/$H_2O$ (6 mL) was stirred overnight at 20° C. under $N_2$. The solution was concentrated under vacuum and acidified to pH 1 with 1N HCl. The resulting tan solid was collected by filtration, washed with $H_2O$ and air dried to yield 114 mg of 3,5-dichloro-2-methyl-4-(3-methyl-4-hydroxy-5-isopropylphenoxy)benzoic acid.

(e) To a stirred DMF solution (5 mL) of crude 3,5-dichloro-2-methyl-4-(3-methyl-4-hydroxy-5-isopropylphenoxy)benzoic acid (114 mg, 0.31 mmol) under $N_2$ was added sequentially EDCI (83 mg, 0.43 mmol), HOBT (80 mg, 0.53 mmol), methyl glycinate hydrochloride (78 mg, 0.62 mmol) and $Et_3N$ (0.13 mL, 0.93 mmol). After stirring for 21 hr at 20° C., detection of starting benzoic acid by LCMS analysis prompted addition of 8 mg of methyl glycinate hydrochloride and 13 mL of $Et_3N$. The reaction was terminated 3 hr later by dilution with 3 mL of 1N HCl and 25 mL of $H_2O$. After extracting the aqueous phase 3× with EtOAc, the combined EtOAc layers were washed 2× with $H_2O$ and 1× with brine prior to drying over $MgSO_4$. Concentration yielded 163 mg of crude glycinamide which was chromatographed on silica gel; 1:4 EtOAc/hexane eluted 96 mg of desired methyl N-(3,5-dichloro-2-methyl-4-(3-methyl-4-hydroxy-5-isopropylphenoxy)benzoyl)glycinate as a beige solid.

(f) A solution of methyl N-(3,5-dichloro-2-methyl-4-(3-methyl-4-hydroxy-5-isopropylphenoxy)benzoyl)glycinate (96 mg, 0.22 mmol) and LiOH $H_2O$ (46 mg, 1.09 mmol) in a 5:1 THF/$H_2O$ (6 mL) was stirred overnight at 20° C. under $N_2$. The solution was concentrated under vacuum and acidified to pH 1 with 1N HCl. After extracting the aqueous phase 3× with EtOAc, the combined EtOAc layers were dried over $MgSO_4$. Concentration yielded 92 mg of crude glycinamide which was purified by reverse phase chromatography (C18 column). Gradient elution with MeCN/$H_2O$ containing 0.1% TFA eluted 72 mg of desired N-(3,5-dichloro-2-methyl-4-(3-methyl-4-hydroxy-5-isopropylphenoxy)benzoyl)glycinic acid.

Example 8

N-[3,5-Dibromo-2-methyl-4-(3-methyl-4-hydroxy-5-isopropylphenoxy)benzoyl]glycine (E8)

Example E8 is prepared by a procedure similar to that described for Example E7.

Example 9

N-[3,5-Dimethyl-2-methyl-4-(3-methyl-4-hydroxy-5-isopropylphenoxy)benzoyl]glycine (E9)

Example E9 is prepared by a procedure similar to that described for Example E7.

Example 10

L-N-[3,5-Dibromo-4-(3-fluoro-4-hydroxy-5-isopropylphenoxy)phenylacetyl]valine (E10)

(a) To a solution of methyl[3,5-dibromo-4-(3-isopropyl-4-methoxyphenoxy)phenyl]acetate (1.0 g, 2.12 mmol) in benzene (150 mL), nitric acid (0.81 mL, 65%) was added drop-wise. The mixture was further stirred for 1 hour at room temperature. The reaction was monitored by TLC (65:35 n-heptane/ethyl acetate) and the reaction mixture was quenched with a saturated aqueous solution of sodium hydrogen carbonate. The resulting organic and aqueous phases were separated and the aqueous phase was extracted with ethyl acetate. The combined organic phase was washed with water, brine, and the organic phase was dried over magnesium sulfate, and concentrated. The crude product was crystallized from methanol to give 1.1 g, (99%) of methyl[3,5-dibromo-4-(5-isopropyl-4-methoxy-3-nitrophenoxy)phenyl]acetate.

(b) Methyl[3,5-dibromo-4-(5-isopropyl-4-methoxy-3-nitrophenoxy)phenyl]acetate (1.1 g, 2.12 mmol) was dissolved in ethanol (50 mL) and sodium hydrosulfite (1.85 g, 10.6 mmol) was added. The reaction mixture was heated at reflux for 48 hours. The reaction monitored by TLC (65:35 n-heptane: EtOAc) and when complete, diluted with ethyl acetate and washed with water and brine. The organic layer was dried over $MgSO_4$ and concentrated. The residue was purified on column (silica gel, n-heptane/EtOAc 1:1) to yield methyl[3,5-dibromo-4-(3-amino-5-isopropyl-4-methoxyphenoxy)phenyl]acetate (457 mg, 44%).

(c) A solution of nitrosonium tetrafluoroborate (121 mg, 1.03 mmol) in dichloromethane (10 mL) was cooled to 0° C. and methyl[3,5-dibromo-4-(3-amino-5-isopropyl-4-methoxy-phenoxy)phenyl]acetate (457 mg, 0.94 mmol) was added. The reaction mixture was stirred at 0° C. for one hour. Dichloromethane was removed by flushing of nitrogen gas and o-xylene (10 mL) was added to the residue. The reaction mixture was heated at reflux for one hour and the organic phase concentrated in vacuo. The residue was purified on column (silica gel, n-heptane/ethyl acetate, gradient elution from 98:2 to 60:40) to give 205 mg (44%) of methyl[3,5-dibromo-4-(3-fluoro-5-isopropyl-4-methoxyphenoxy)phenyl]acetate.

(d) To a solution of methyl[3,5-dibromo-4-(3-fluoro-5-isopropyl-4-methoxyphenoxy)phenyl]acetate (205 mg, 0.42 mmol) in tetrahydrofuran (30 mL), lithium hydroxide (30 mL, 1N) was added. The reaction mixture was stirred over night at room temperature, acidified with hydrochloric acid (1 N) and the aqueous and organic phase separated. The aqueous phase extracted with ethyl acetate. The combined organic phase was washed with water, dried over magnesium sulfate and concentrated in vacuo. The residue was purified on column (silica gel, chloroform/methanol/acetic acid 98:2:0.3) to give 210 mg (99%) of 3,5-dibromo-4-(3-fluoro-5-isopropyl-4-methoxyphenoxy)phenylacetic acid.

(e) L-valine methyl ester hydrochloride (148 mg, 0.88 mmol) and triethylamine (134 mg, 1.32 mmol) was added to a stirred mixture of 3,5-dibromo-4-(3-fluoro-5-isopropyl-4-methoxyphenoxy)phenylacetic acid (210 mg, 0.44 mmol)), EDCI (169 mg, 0.88 mmol), HOBt (135 mg, 0.88 mmol) in N,N-dimethylformamide (25 mL). The reaction mixture was stirred for 24 hours at room temperature, poured out in a mixture of hydrochloric acid (1 N, 5 mL) and water (30 mL), and extracted with ethyl acetate. The collected organic phases were dried, the organic phase concentrated and the residue purified on column (silica gel, n-heptane/ethyl acetate, gradient elution from 98:2 to 60:40) to give 224 mg (86%) of L-methyl-N-[3,5-dibromo-4-(3-fluoro-5-isopropyl-4-methoxyphenoxy)phenylacetyl]valinate.

(f) Boron trifluoride dimethyl sulfide (4.0 mL) was added at room temperature to a stirred solution of L-methyl-N-[3,5-dibromo-4-(3-fluoro-5-isopropyl-4-methoxy-phenoxy) phenylacetyl]valine (224 mg, 0.38 mmol) in dichloromethane (25 mL). The reaction mixture was stirred at room temperature for 24 hours, poured out in water and extracted with ethyl acetate. The combined organic phases were washed with water, concentrated and the resulting residue purified on column (silica gel, chloroform/methanol/ acetic acid 98:2:0.3) to give 93 mg (44%) of L-N-[3,5-dibromo-4-(3-fluoro-4-hydroxy-5-isopropylphenoxy)phenylacetyl]valine.

Example 11

D-N-[3,5-Dibromo-4-(3-chloro-4-hydroxy-5-isopropylphenoxy)phenylacetyl]phenylglycine (E11)

(a) To a stirred solution of 3,5-dibromo-4-(3-isopropyl-4-methoxyphenoxy)phenylacetic acid (1.5 g, 3.4 mmol) in acetic acid (40 mL) at room temperature was added benzyltrimethylammonium tetrachloroiodate (1.42 g, 3.4 mmol). The reaction mixture was stirred for one hour and was filtered. The filtrate was concentrated, and the product was extracted with ethyl acetate, washed with saturated $NaHCO_3$ (aq), NaCl (aq), and dried over $MgSO_4$ and concentrated in vacuo. The residue was purified on column (silica gel, chloroform/methanol/acetic acid 98:2:0.3) to give 802 mg (50%) of 3,5-dibromo-4-(3-chloro-4-hydroxy-5-isopropylphenoxy)phenylacetic acid.

(b) D-phenylglycine methyl ester hydrochloride (674 mg, 3.34 mmol) and triethylamine (507 mg, 5.02 mmol) was added to a stirred mixture of 3,5-dibromo-4-(3-chloro-4-hydroxy-5-isopropylphenoxy)phenylacetic acid (800 mg, 1.7 mmol), EDCI (641 mg, 3.34 mmol), HOBt (512 mg, 3.34 mmol) in N,N-dimethylformamide (100 mL). The reaction mixture was stirred for 24 hours at room temperature, poured out into a mixture of hydrochloric acid (1 N, 5 mL) and water (30 mL), and extracted with ethyl acetate. The collected organic phases were dried, the organic phase concentrated and the residue purified on column (silica gel, n-heptane/ethyl acetate, gradient elution from 98:2 to 60:40) to give 800 mg (75%) of D-methyl-N-[3,5-dibromo-4-(3-chloro-5-isopropyl-4-methoxyphenoxy)phenylacetyl]phenylglycinate.

(c) Boron trifluoride dimethyl sulfide (10 mL) was added at room temperature to a stirred solution of D-methyl-N-[3, 5-dibromo-4-(3-chloro-5-isopropyl-4-methoxyphenoxy) phenylacetyl]phenylglycinate (800 mg, 1.3 mmol) and dichloromethane (80 mL). The reaction mixture was stirred at room temperature for 24 hours, poured out in water and extracted with ethyl acetate. The combined organic phases were washed with water, concentrated and the resulting residue purified on column (silica gel, chloroform/methanol/ acetic acid 98:2:0.3) to give 350 mg (44%) of D-N-[3,5-dibromo-4-(3-chloro-4-hydroxy-5-isopropylphenoxy)phenylacetyl]phenylglycine.

Example 12

L-N-[3,5-Dibromo-4-(4-hydroxy-3-isopropyl-5-methylphenoxy)phenylacetyl]valine (E12)

(a) Methyl[3,5-dibromo-4-(4-hydroxy-3-isopropylphenoxy)phenyl]acetate (2.0 g, 4.4 mmol), $SnCl_4$ (25 µl, 0.2 mmol), trioctyl amine (0.77 mL, 1.76 mmol) and toluene (15 mL) were mixed in a reaction vial. After 20 minutes stirring at room temperature, paraformaldehyde (0.264 g, 8.8 mmol) was added to the reaction solution. The reaction vial was sealed and the temperature increased to 105° C. After 20 hours stirring, the reaction was quenched with ice-water and acidified with hydrochloric acid (1 N). Extraction with ethyl acetate, washing with brine, drying over $Na_2SO_4$ and concentration gave the crude product. The residue was purified on column (silica, gradient elution: n-heptane/ethyl acetate from 1:0 to 4:1) to give 1.08 g (51%) of methyl[3,5-dibromo-4-(3-formyl-4-hydroxy-5-isopropylphenoxy)phenyl]acetate.

(b) Triethylsilane was added to a mixture of methyl[3,5-dibromo-4-(3-formyl-4-hydroxy-5-isopropylphenoxy)phenyl]acetate (243 mg, 0.5 mmol) and trifluoroacetic acid (10 mL) at room temperature. After 12 hours stirring, the reaction mixture was concentrated via co-evaporated with toluene. The residue was purified on column (silica, gradient elution: n-heptane/ethyl acetate from 9:1 to 7:3) to give 197 mg (84%) of methyl[3,5-dibromo-4-(4-hydroxy-3-isopropyl-5-methylphenoxy)phenyl]acetate.

(c) A mixture of methyl[3,5-dibromo-4-(4-hydroxy-3-isopropyl-5-methylphenoxy)phenyl]acetate (194 mg, 0.41 mmol) and lithium hydroxide (20 mL, 1 N) in tetrahydrofuran (10 mL) was stirred for 10 hours at room temperature. The reaction mixture was neutralized with cold aqueous hydrochloric acid followed by extraction with ethyl acetate (3×30 mL). The combined organic layers were washed with water (4×25 mL) and co-evaporated with acetonitrile. The residue was purified on column (silica, gradient elution: chloroform/methanol/acetic acid from 1:0:0 to 90:10:1) to yield 169 mg (90%) of 3,5-dibromo-4-(4-hydroxy-3-isopropyl-5-methylphenoxy)phenyl]acetic acid.

(d) A mixture of compound 3,5-dibromo-4-(4-hydroxy-3-isopropyl-5-methylphenoxy)phenylacetyl]acetic acid (0.44 g, 0.96 mmol), L-valine methylester (322 mg, 1.92 mmol), 3-ethyl-1-[3-(dimethylamino)propyl]carbodiimide hydrochloride (EDCI) (174 mg, 1.44 mmol) and N,N-dimethyl-formamide (9 mL) was stirred for 5 minutes at room temperature, where after 1-hydroxybenzotriazole hydrate (HOBt) (220 mg, 1.44 mmol) and triethylamine (0.401 mL, 12.88 mmol) were added. After 16 hours bromotripyrrolidinophosphonium hexafluorophosphate (0.2 g, 0.43 mmol) was added. After 1.75 hours of stirring at room temperature the obtained reaction mixture was diluted with water (10 mL) and hydrochloric acid (10 ml, 1 N), the aqueous layer extracted with ethyl acetate (3×20 mL) and the combined organic layers washed with brine (40 mL). After drying over $Na_2SO_4$, filtration and concentration the crude product was filtrated through a short silica pad. Purification on a chromatotron (silica, 4 mm, n-heptane/ethyl acetate 6:4) gave 240 mg (44%) of L-methyl-N-[3,5-dibromo-4-(4-hydroxy-3-isopropyl-5-methylphenoxy)phenylacetyl]valinate.

(e) To a stirred solution of compound L-methyl-N-[3,5-dibromo-4-(4-hydroxy-3-isopropyl-5-methyl-phenoxy)phenylacetyl]valinate (240 mg, 0.42 mmol) and tetrahydrofuran (4 mL) was added lithium hydroxide (4 mL, 1N). After one hour stirring the pH of reaction was adjusted to 1 with hydrochloric acid (1 N). The organic phase was concentrated in vacuo. The residue was extracted with ethyl acetate and the combined organic phases were dried over $Na_2SO_4$ and concentrated. The residue was purified on column (MPLC, silica, gradient elution: chloroform/methanol/acetic acid from 1:0:0 to 98:2:0.3) to yield compound L-N-[3,5-dibromo-4-(4-hydroxy-3-isopropyl-5-methyl-phenoxy)phenylacetyl]valine as a white solid (0.14 g, 60%). LC-MS (ES–1): m/z 554.

Example 13

L-N-[3,5-Dibromo-4-(4-hydroxy-3-isopropyl-5-methylphenoxy)phenylacetyl]phenylglycine (E13)

(a) A solution of 3,5-dibromo-4-(4-hydroxy-3-isopropyl-5-methylphenoxy)phenylacetic acid (18 mg, 0.04 mmol), diisopropylethylamine (33 μl, 0.2 mmol), bromotripyrrolidinophosphonium hexafluorophosphate (22 mg, 0.05 mmol), 1-hydroxybenzotriazole hydrate (7 mg, 0.05 mmol), D-phenylglycine methylester (16 mg, 0.08 mmol) and dichloromethane (1 mL) was stirred for 30 minutes at room temperature. There after was the reaction washed with hydrochloric acid (2 ml, 1 N) and the aqueous layer was extracted with chloroform (3×2 mL). The combined organic layers were dried over $Na_2SO_4$ and concentrated in vacuo. Purification on a column (silica, gradient elution: n-heptane/ethyl acetate from 4:1 to 7:3) yielded 16 mg (74%) of L-methyl-N-[3,5-dibromo-4-(4-hydroxy-3-isopropyl-5-methylphenoxy)phenylacetyl]phenylglycinate.

(b) L-Methyl-N-[3,5-dibromo-4-(4-hydroxy-3-isopropyl-5-methylphenoxy)phenylacetyl]phenylglycinate (15 mg, 0.025 mmol) was dissolved in tetrahydrofuran (0.5 mL) and the resulting solution was treated with aqueous lithium hydroxide (0.5 mL, 1 N) for 1 hour at room temperature. The reaction was acidified with hydrochloric acid (1 N) and the organic phase was removed in vacuo. The residue was extracted with ethyl acetate (3×5 mL) and the combined organic phases were dried over $Na_2SO_4$ before concentration in vacuo. The residue was purified on column (HPLC, C8, gradient elution: acetonitrile/water (0.5% formic acid) from 1:4 to 1:0) to give L-N-[3,5-dibromo-4-(4-hydroxy-3-isopropyl-5-methylphenoxy)phenylacetyl]phenylglycine as a white solid (6 mg, 41%). LC-MS (ES–1): m/z 588.

Example 14

L-N-[3,5-Dibromo-4-(3,5-dimethyl-4-hydroxyphenoxy)phenylacetyl]-phenylglycine (E14)

(a) Bis-(4-methoxyphenyl) iodonium tetrafluoroborate (5.48 g, 12.8 mmol) and cupper powder (1.25 g, 19.6 mmol) was suspended in dichloromethane (25 mL) and the resulting suspension was cooled to 0° C. While stirring, a solution of methyl(3,5-dibromo-4-hydroxyphenyl)acetate (3.19 g, 9.8 mmol), triethylamine (1.64 mL, 11.8 mmol) and dichloromethane (35 mL) was added to the suspension covered by aluminum foil. After 20 hours stirring in the dark at room temperature the crude reaction mixture was washed with hydrochloric acid (1 N) and a phase separator (IST) was used to separate the two phases. The remaining acidic aqueous phase was extracted by chloroform and the collected organic phases were concentrated in vacuo. The residue was purified on column (MPLC, silica gel, gradient elution: n-heptane/ethyl acetate from 1:0 to 4:1) to give 2.5 g (45%) of methyl[3,5-dibromo-4-(4-hydroxyphenoxy)phenyl]acetate.

(b) $BF_3$—$SMe_2$ (24 mL, 228 mmol) was added to a stirred solution of methyl[3,5-dibromo-4-(4-methoxyphenoxy)phenyl]acetate (2.5 g, 5.8 mmol) and dichloromethane (50 mL) at 0° C. The reaction mixture was stirred for 20 hours at room temperature and subsequently quenched with ice water (50 mL). The two layers were separated with a phase separator and the remaining water phase was extracted with ethyl acetate. Filtration through a silica pad gave the crude 3,5-dibromo-4-(4-hydroxyphenoxy)phenylacetic acid. The residue was dissolved in methanol (40 mL) and thionyl chloride (4 mL) was added carefully to the reaction. After 1.5 hours of heating at reflux, the organic phase was removed in vacuo and the residue was dissolved in chloroform. The organic phase was washed with water and concentrated to give methyl[3,5-dibromo-4-(4-hydroxyphenoxy)phenyl]acetate as beige solid (1.8 g, 75%).

(c) Hexamethylenetetramine (262 mg, 1.87 mmol) was added to a solution of methyl[3,5-dibromo-4-(4-hydroxyphenoxy)phenyl]acetate (370 mg, 0.89 mmol) and trifluoroacetic acid (1.5 mL). The reaction mixture was stirred for 16 hours at 95° C. before cooling to room temperature. Hydrochloric acid (3 mL, 2 N) was added and the reaction mixture was stirred for one hour and extracted with chloroform. The organic phase was concentrated in vacuo and dissolved in ethyl acetate. The organic phase was washed with hydrochloric acid (2 N), water and brine, dried over $Na_2SO_4$ and concentrated. The residue was purified on a column (MPLC, silica, gradient eluent: n-heptane/ethyl acetate from 1:0 to 4:1) to give yielded methyl[3,5-dibromo-4-(3-formyl-4-hydroxyphenoxy)phenyl]acetate as a white solid (150 mg, 38%).

(d) A mixture of compound methyl[3,5-dibromo-4-(3-formyl-4-hydroxyphenoxy)phenyl]acetate (250 mg, 0.56 mmol) and trifluoroacetic acid (5.5 mL) was treated with triethylsilane (0.34 mL, 2.13 mmol) and the reaction mixture was stirred for 16 hours at room temperature. The reaction was concentrated and co-evaporated (toluene, dichloromethane), which gave a residue that was filtrated through a pad of silica. Purification on a column (MPLC, silica, gradient elution: n-heptane/ethyl acetate from 1:0 to 4:1) gave 110 mg (46%) of methyl[3,5-dibromo-4-(4-hydroxy-3-methyl-phenoxy)phenyl]acetate.

(e) A solution of methyl[3,5-dibromo-4-(4-hydroxy-3-methyl-phenoxy)phenyl]acetate (110 mg, 0.26 mmol), hexamethylenetetramine (77 mg, 0.55 mmol) and trifluoroacetic acid (2.5 mL) was stirred at 100° C. for 20 hours. The reaction solution was diluted with hydrochloric acid (5 mL, 2 N) and the resulting mixture was stirred at room temperature for 30 minutes before it was extracted with chloroform. The organic phase was concentrated and diluted with ethyl acetate, and washed with hydrochloric acid (2×10 mL, 2 N), water (10 mL) and brine (10 mL). The organic layer was dried over $Na_2SO_4$, concentrated and filtrated through a silica pad to give 60 mg (50%) of methyl[3,5-dibromo-4-(3-formyl-4-hydroxy-5-methylphenoxy)phenyl]acetate.

(f) To a stirred mixture of methyl[3,5-dibromo-4-(3-formyl-4-hydroxy-5-methyl-phenoxy)phenyl]acetate (60 mg, 0.13 mmol) and trifluoroacetic acid (1.5 mL), triethylsilane (62 µl, 0.39 mmol) was added. The reaction mixture was stirred at room temperature for 20 hours, the organic phase concentrated and the residue was co-evaporated (toluene) to give 60 mg of crude methyl[3,5-dibromo-4-(3,5-dibromo-4-hydroxyphenoxy)phenyl]acetate. The crude product was used in next step. Lithium hydroxide (1.5 ml, 1N) was added to a stirred solution of crude methyl[3,5-dibromo-4-(3,5-dibromo-4-hydroxyphenoxy)phenyl]acetate and tetrahydrofuran (1.5 mL). The resulting mixture was stirred for 2 hours at room temperature, acidified with hydrochloric acid (1 N) and extracted with ethyl acetate. The organic phase was dried over $Na_2SO_4$ and concentrated in vacuo. The residue was purified on column (HPLC, C8, gradient eluent: acetonitrile/water (0.5% formic acid) from 1:4 to 1:0) to give 16 mg (14% for both steps) of 3,5-dibromo-4-(3,5-dibromo-4-hydroxyphenoxy)phenylacetic acid.

(g) 3,5-Dibromo-4-(3,5-dibromo-4-hydroxyphenoxy) phenylacetic acid (16 mg, 0.037 mmol), diisopropylethyl amine (33 µl, 0.2 mmol), bromotripyrrolidinophosphonium hexafluorophosphate (21 mg, 0.044 mmol), 1-hydroxybenzotriazole hydrate (7 mg, 0.05 mmol), D-phenylglycine methylester (15 mg, 0.074 mmol) and dichloromethane (0.5 mL) were mixed and stirred for 1 hour at room temperature, and thereafter stored at 4° C. for 20 hours. The reaction mixture was washed with hydrochloric acid (1 N) and the remaining aqueous layer extracted with chloroform. The combined organic layers were concentrated in vacuo and the residue was purified on a column (silica, eluent: chloroform) to give 10 mg (47%) of L-methyl-N-[3,5-dibromo-4-(3,5-dimethyl-4-hydroxyphenoxy)phenylacetyl]phenylglycinate.

(h) L-Methyl-N-[3,5-dibromo-4-(3,5-dimethyl-4-hydroxyphenoxy)phenylacetyl]-phenylglycinate (10 mg, 0.017 mmol) was dissolved in tetrahydrofuran (0.25 mL) and lithium hydroxide (0.25 mL, 1 N) was added. The reaction mixture was stirred for 1 hour at room temperature and 1 M hydrochloric acid (1 N) was added subsequently until pH reached 1. The obtained mixture was extracted with ethyl acetate and the combined organic layers were dried over $Na_2SO_4$. After concentration and purification on preparative TLC (silica, eluent: chloroform/methanol/acetic acid 9:1: 0.1), 5 mg (52%) of L-N-[3,5-Dibromo-4-(3,5-dimethyl-4-hydroxyphenoxy)phenylacetyl]phenylglycine was obtained. LC-MS (ES-1): m/z 560.

The compounds of Examples 1–6 exhibit binding affinities to the thyroid receptor beta in the range of $IC_{50}$ of 1.0 to 100 nM.

The invention claimed is:

1. A compound selected from the group consisting of:
   N-[3,5-Dichloro-4-(4-hydroxy-3-isopropyl-5-methylphenoxy)benzoyl]glycine (E1);
   N-[3,5-Dichloro-4-(3-bromo-4-hydroxy-5-isopropylphenoxy)benzoyl]glycine (E2);
   N-[3,5-Dichloro-4-(2-bromo-4-hydroxy-5-isopropylphenoxy)benzoyl]glycine (E3);
   N-[3,5-Dichloro-4-(3-chloro-4-hydroxy-5-isopropylphenoxy)benzoyl]glycine (E4);
   N-[3,5-Dichloro-4-(3-cyano-4-hydroxy-5-isopropylphenoxy)benzoyl]glycine (E5);
   N-[3,5-Dichloro-4-(3-fluoro-4-hydroxy-5-isopropylphenoxy)benzoyl]glycine (E6);
   N-[3,5-Dichloro-2-methyl-4-(3-methyl-4-hydroxy-5-isopropylphenoxy)benzoyl]glycine (E7);
   L-N-[3,5-Dibromo-4-(3-fluoro-4-hydroxy-5-isopropylphenoxy)phenylacetyl]valine (E10);
   D-N-[3,5-Dibromo-4-(3-chloro-4-hydroxy-5-isopropylphenoxy)phenylacetyl]phenylglycine (E11);
   L-N-[3,5-Dibromo-4-(4-hydroxy-3-isopropyl-5-methylphenoxy)phenylacetyl]valine (E12);
   L-N-[3,5-Dibromo-4-(4-hydroxy-3-isopropyl-5-methylphenoxy)phenylacetyl]phenylglycine (E13);
   L-N-[3,5-Dibromo-4-(3,5-dimethyl-4-hydroxyphenoxy) phenylacetyl]-phenylglycine (E14);
   N-[3,5-Dibromo-2-methyl-4-(3-methyl-4-hydroxy-5-isopropylphenoxy)benzoyl]glycine (E8); and
   N-[3,5-Dimethyl-2-methyl-4-(3-methyl-4-hydroxy-5-isopropylphenoxy)benzoyl]glycine (E9).

2. A pharmaceutical composition comprising an effective amount of a compound according to claim 1 or a pharmaceutically effective salt thereof, together with a pharmaceutically acceptable carrier.

3. A process for making a pharmaceutical composition comprising combining a compound according to claim 1 and a pharmaceutically acceptable carrier.

4. A pharmaceutical composition comprising a compound according to claim 1 and at least one additional therapeutic agent selected from the group consisting of anti-diabetic agents, anti-osteoporosis agents, anti-obesity agents, growth promoting agents, anti-inflammatory agents, anti-anxiety agents, anti-depressants, anti-hypertensive agents, cardiac glycosides, cholesterol/lipid lowering agents, appetite suppressants, bone resorption inhibitors, thyroid mimetics, anabolic agents, anti-tumor agents and retinoids.

5. The pharmaceutical composition of claim 4 wherein said additional therapeutic agent is an anti-diabetic agent selected from the group consisting of a biguanide, a glucosidase inhibitor, a meglitinide, a sulfonylurea, a thiazolidinedione, a PPAR-alpha agonist, a PPAR-gamma agonist, a PPAR alpha/gamma dual agonist, an SGLT2 inhibitor, a glycogen phosphorylase inhibitor, an aP2 inhibitor, a glucagon-like peptide-1 (GLP-1), a dipeptidyl peptidase IV inhibitor and insulin.

6. The pharmaceutical composition of claim 4 wherein said additional therapeutic agent is an anti-diabetic agent selected from the group consisting of metformin, glyburide, glimepiride, glipyride, glipizide, chlorpropamide, gliclazide, acarbose, miglitol, troglitazone, pioglitazone, englitazone, darglitazone, rosiglitazone and insulin.

7. The pharmaceutical composition of claim 4 wherein said additional therapeutic agent is an anti-obesity agent is selected from the group consisting of an aP2 inhibitor, a PPAR gamma antagonist, a PPAR delta agonist, a beta 3 adrenergic agonist, a lipase inhibitor, a serotonin reuptake inhibitor, a cannabinoid-I receptor antagonist and an anorectic agent.

8. The pharmaceutical composition of claim 4 wherein said additional therapeutic agent is a hypolipidemic agent selected from the group consisting of a thiazolidinedione, an MTP inhibitor, a squalene synthetase inhibitor, an HMG CoA reductase inhibitor, a fibric acid derivative, an ACAT inhibitor, a cholesterol absorption inhibitor, an ileal $Na^+$/bile cotransporter inhibitor, a bile acid sequestrant and a nicotinic acid or a derivative thereof.

9. A pharmaceutical composition which functions as a selective agonist of the thyroid hormone receptor comprising a compound as defined in claim 1.

* * * * *

UNITED STATES PATENT AND TRADEMARK OFFICE
CERTIFICATE OF CORRECTION

PATENT NO.       : 7,153,997 B2                                              Page 1 of 1
APPLICATION NO.  : 10/520902
DATED            : December 26, 2006
INVENTOR(S)      : Neeraj Garg et al.

It is certified that error appears in the above-identified patent and that said Letters Patent is hereby corrected as shown below:

In the second line of claim 7 at column 39, line 19, the last word in column 39, "is", should be deleted from the second line of claim 7. The second and third lines of claim 7 will then correctly read as follows:

--said additional therapeutic agent is an anti-obesity agent
   selected from the group consisting of an aP2 inhibitor, a--.

Signed and Sealed this

Tenth Day of July, 2007

JON W. DUDAS
*Director of the United States Patent and Trademark Office*